United States Patent
Ito et al.

(10) Patent No.: US 9,977,042 B2
(45) Date of Patent: May 22, 2018

(54) OBJECT MOVING DEVICE

(71) Applicant: YAMAHA HATSUDOKI KABUSHIKI KAISHA, Iwata-shi, Shizuoka-ken (JP)

(72) Inventors: Saburo Ito, Shizuoka (JP); Yukimasa Osada, Shizuoka (JP); Yohei Izume, Shizuoka (JP)

(73) Assignee: YAMAHA HATSUDOKI KABUSHIKI KAISHA, Shizuoka-ken (JP)

( * ) Notice: Subject to any disclaimer, the term of this patent is extended or adjusted under 35 U.S.C. 154(b) by 0 days. days.

(21) Appl. No.: 15/317,661

(22) PCT Filed: Jun. 17, 2014

(86) PCT No.: PCT/JP2014/066047
§ 371 (c)(1),
(2) Date: Dec. 9, 2016

(87) PCT Pub. No.: WO2015/193970
PCT Pub. Date: Dec. 23, 2015

(65) Prior Publication Data
US 2017/0131308 A1 May 11, 2017

(51) Int. Cl.
*G01N 35/02* (2006.01)
*G01N 35/04* (2006.01)
(Continued)

(52) U.S. Cl.
CPC .......... *G01N 35/026* (2013.01); *G01N 21/59* (2013.01); *G01N 35/0099* (2013.01);
(Continued)

(58) Field of Classification Search
CPC ................. G01N 2035/103; G01N 2035/0099
See application file for complete search history.

(56) References Cited

U.S. PATENT DOCUMENTS 5,275,951 A * 1/1994 Chow ................... B01L 3/0262
137/392
2003/0082818 A1 5/2003 Bahnson et al.
2013/0280143 A1 10/2013 Zucchelli et al.

FOREIGN PATENT DOCUMENTS

EP    3 081 632 A1    10/2016
JP    H06-507499 A    8/1994
(Continued)

OTHER PUBLICATIONS

The extended European search report issued by the European Patent Office dated May 16, 2017, which corresponds to European Patent Application No. 14895075.1-1553 and is related to U.S. Appl. No. 15/317,661.
(Continued)

*Primary Examiner* — P. Kathryn Wright
(74) *Attorney, Agent, or Firm* — Studebaker & Brackett PC

(57) ABSTRACT

An object moving device includes: a first drive mechanism configured to move a head unit in a first direction and in a second direction; a second drive mechanism configured to move an illumination unit in the first direction; and a third drive mechanism configured to move a camera unit in the first direction. A control unit controls the first drive mechanism to move the head unit on a first path. The control unit controls the second and third drive mechanisms to move the illumination unit and the camera unit on the first path between the first container and the second container. When the head unit and the illumination unit interfere with each other on the first path, the control unit implements control such that the head unit moves in the second direction and the head units moves in the first direction on a second path parallel to the first path.

7 Claims, 27 Drawing Sheets

(51) Int. Cl.
　　　*G01N 35/10*　　　(2006.01)
　　　*G01N 35/00*　　　(2006.01)
　　　*G01N 21/59*　　　(2006.01)
(52) U.S. Cl.
　　　CPC ..... *G01N 35/1002* (2013.01); *G01N 35/1074* (2013.01); *G01N 2035/0434* (2013.01); *G01N 2201/062* (2013.01)

(56) References Cited

FOREIGN PATENT DOCUMENTS

| | | |
|---|---|---|
| JP | H11-287812 A | 10/1999 |
| JP | 2005-304303 A | 11/2005 |
| JP | 2009-034013 A | 2/2009 |
| JP | 2013-543984 A | 12/2013 |
| WO | 2013/114430 A1 | 8/2013 |

OTHER PUBLICATIONS

International Search Report issued in PCT/JP2014/066047; dated Sep. 22, 2014.

\* cited by examiner

OBJECT MOVING DEVICE

CROSS REFERENCE TO RELATED APPLICATIONS

This application claims benefit of priority to International Patent Application No. PCT/JP2014/066047 filed Jun. 17, 2014, the entire content of which is incorporated herein by reference.

TECHNICAL FIELD

The present disclosure relates to a moving device configured to move an object, such as a cell aggregate, from one container to another container.

BACKGROUND

Moving devices configured to move a certain object from one container to another container are required in various technical fields. For example, there is a moving device configured such that, in a case where there are a first container storing a large number of moving objects such as compact parts, organic or inorganic fragments or particles, and cells, and a second container receiving the moving objects, some of the moving objects are extracted from the first container and moved to the second container.

Japanese Unexamined Patent Publication No. 2009-34013 discloses a technology of sucking a cell aggregate, which is a moving object, from a dispenser well (first container) with use of a suction tip (micropipette) and discharging the sucked cell aggregate to a cell Petri dish (second container). In order to observe the cell aggregate present in the first container or the second container, it may be required to take an image of the cell aggregate with a camera under proper illumination.

In the work of moving an object such as a cell aggregate, there has been a requirement for highly automating a series of work operations including the object moving operation and the object imaging operation. At present, however, these works are manually implemented in most cases or are implemented by using a simple moving device including only a suction mechanism for sucking an object and a suction tip movement mechanism. It cannot therefore be said that the movement work has high efficiency at present.

SUMMARY

It is an object of the present disclosure to make a movement work efficient in a moving device that is required to move an object from one container to another container and image the object in the containers with a camera.

An object moving device according to one aspect of the present disclosure includes: a base; a head unit arranged above the base and including a head that is movable in an up-down direction; an illumination unit arranged above the base and including a light source emitting illumination light; a camera unit arranged below the base and including a camera acquiring an image under the illumination light; and a first drive mechanism configured to move the head unit in a first direction that extends in a horizontal direction and in a second direction that is orthogonal to the first direction in the horizontal direction; a second drive mechanism configured to move the illumination unit in the first direction; a third drive mechanism configured to move the camera unit in the first direction; a control unit configured to control operations of the first, second, and third drive mechanisms; and a movement line including a plurality of workplaces incorporated in the base and arranged in the first direction, the plurality of workplaces including a first container configured to store a moving object therein and a second container configured to receive the moving object.

The control unit is configured to: control the first drive mechanism to move the head unit on a first path along the movement line in order to implement at the plurality of workplaces works including a work for moving the moving object between the first container and the second container with use of the head; control the second and third drive mechanisms to move the illumination unit and the camera unit between the first container and the second container on the first path in order to image the first container and the second container; and control, when the head unit and the illumination unit interfere with each other on the first path, the first drive mechanism to move the head unit in the second direction and move the head unit in the first direction on a second path that is side by side with the first path.

Objects, features and advantages of the present disclosure become more apparent from the following detailed description and the accompanying drawings.

DETAILED DESCRIPTION

An object moving device according to an embodiment of the present disclosure is now described in detail with reference to the accompanying drawings. In this embodiment, the case where a moving object is a biological cell, in particular, a cell aggregate, is described. Note that the moving object is not limited to a cell aggregate, and may be a compact electronic or mechanical part, an organic or inorganic fragment or particle, or a pellet.

Figure 1:
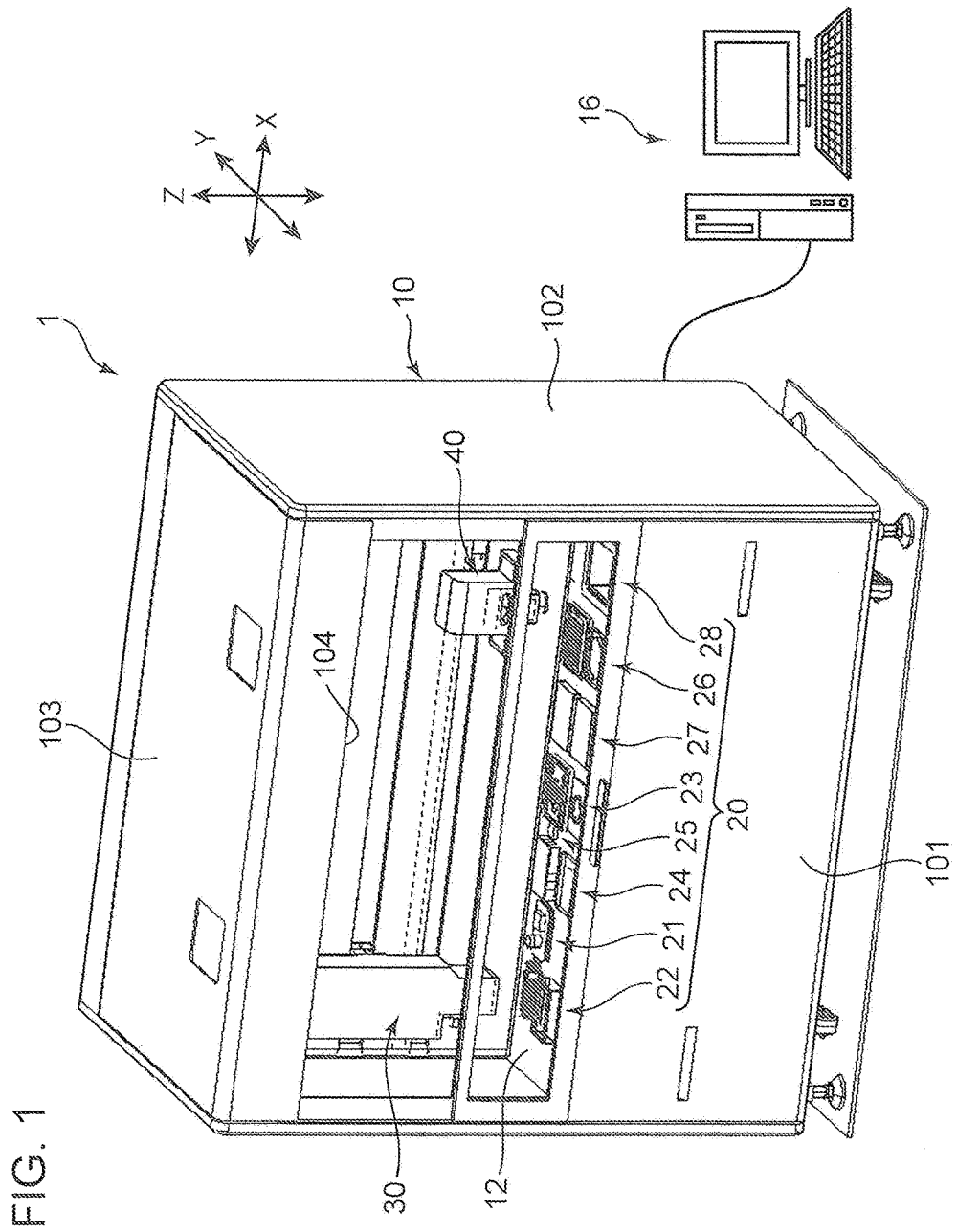
FIG. 1 is a perspective view illustrating an appearance of a moving device according to an embodiment of the present disclosure.

FIG. 1 is a perspective view illustrating an appearance of a moving device 1 for cells according to the embodiment of the present disclosure. The moving device 1 includes an apparatus main body 10, and a control unit 16 including a personal computer, a control board, and the like and configured to control respective operations of units of the apparatus main body 10. The apparatus main body 10 is covered with a box-shaped outer cover, specifically, a front cover 101, side covers 102, a top cover 103, and a rear cover (not shown). An opening portion 104 is provided in an upper part of the front cover 101. The inside of the apparatus main body 10 is exposed through the opening portion 104. The opening portion 104 is covered with a transparent cover. The control unit 16 is communicably connected to the apparatus main body 10.

Figure 2:
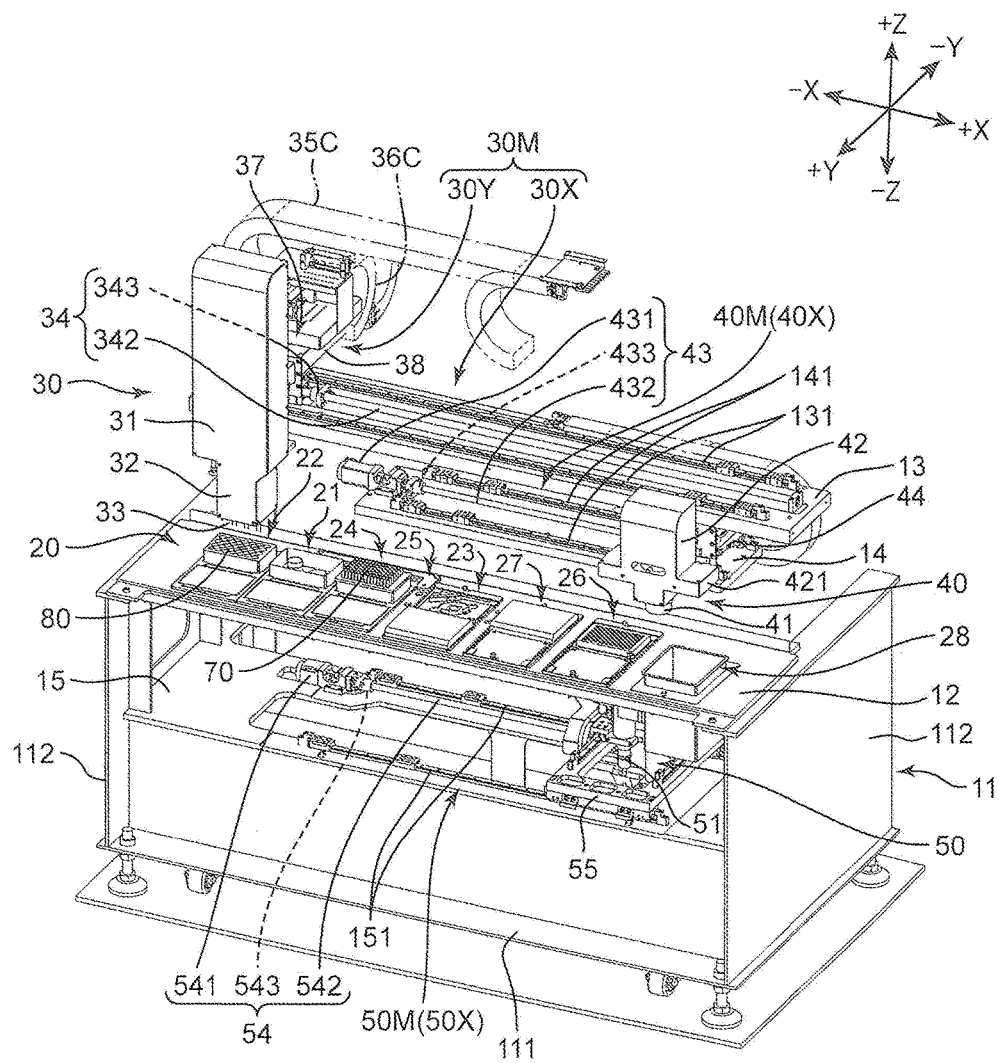
FIG. 2 is a perspective view of the moving device with an outer cover removed.

FIG. 2 is a perspective view of the moving device 1 (apparatus main body 10) with the outer cover removed. In FIG. 2, the directions X, Y, and Z are indicated. In the following description, the X direction is the left-right direction (first direction extending in the horizontal direction), the Y direction is the front-back direction (second direction), and the Z direction is the up-down direction, and +X is rightward, −X is leftward, +Y is frontward, −Y is backward, +Z is upward, and −Z is downward.

Figure 3:
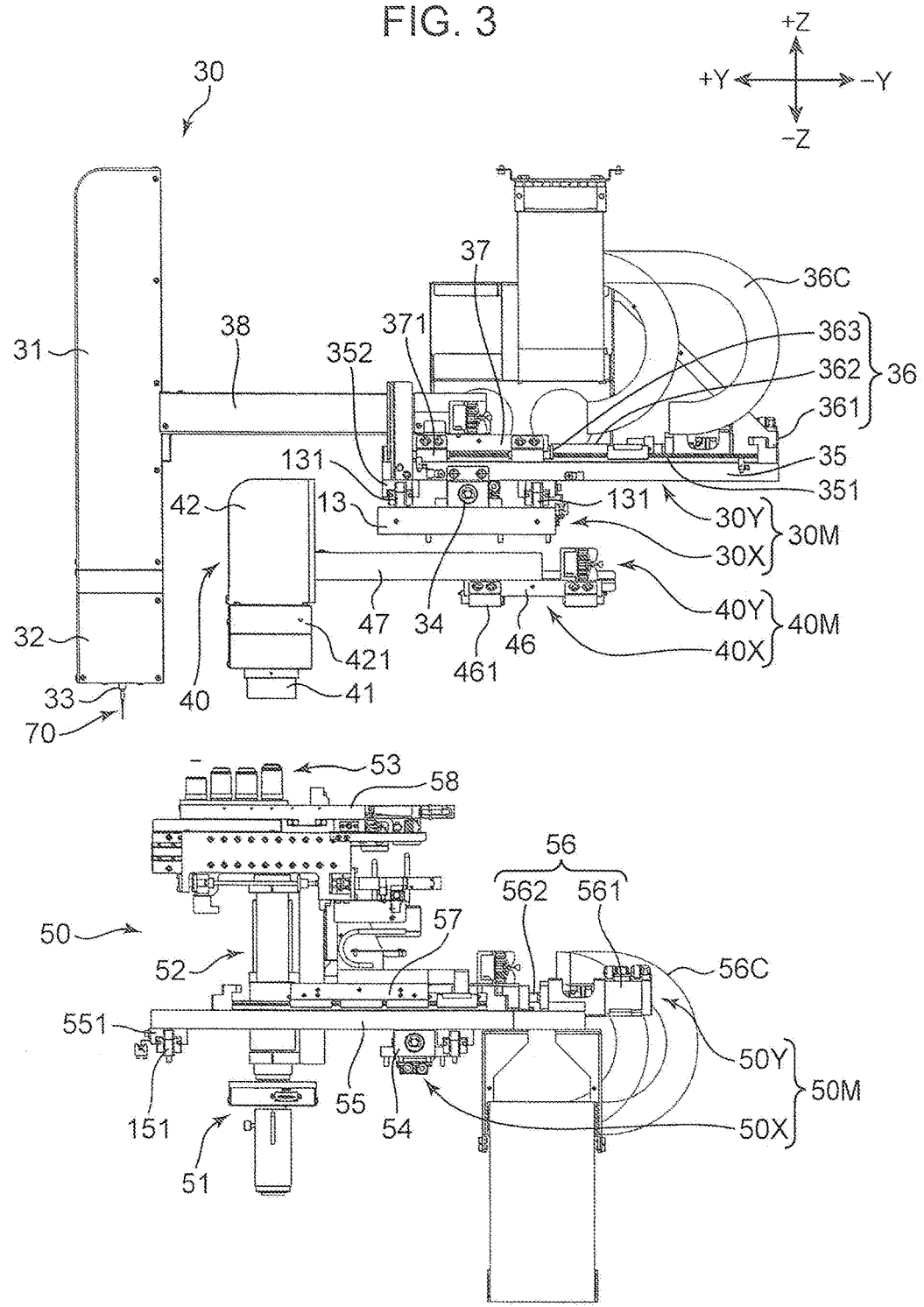
FIG. 3 is a side view of a head unit, an illumination unit, and a camera unit.

The moving device 1 includes a support frame 11, a base 12 supported by the support frame 11, a cell movement line 20 incorporated in the base 12, a head unit 30 and an illumination unit 40 that are arranged above the base 12, and a camera unit 50 arranged below the base 12. FIG. 3 is a side view of the head unit 30, the illumination unit 40, and the camera unit 50.

The moving device 1 further includes a head unit drive device 30M (first drive mechanism) configured to move the head unit 30 in the left-right and front-back directions, an illumination unit drive device 40M (second drive mechanism) configured to move the illumination unit 40 in the left-right and front-back directions, and a camera unit drive device 50M (third drive mechanism) configured to move the camera unit 50 in the left-right and front-back directions. The control unit 16 controls the operations of the drive units 30M, 40M, and 50M, thereby controlling the movement of the head unit 30, the illumination unit 40, and the camera unit 50 in the left-right and front-back directions.

The support frame 11 includes a base frame 111 and a pair of side frames 112. The base frame 111 is a rectangular frame located at the lowermost layer of the moving device 1. A wheel and an adjuster foot are mounted at each of the four corners of a lower surface of the base frame 111. The side frames 112 are frames that protrude upward from both lateral ends of the base frame 111, respectively. Lateral end portions of the base 12 are supported by upper edges of the two side frames 112, respectively.

The base 12 is a rectangular flat plate which has a predetermined rigidity, which is formed of a translucent material in part or in its entirety, and which has substantially the same size as the base frame 111 in top view. In this embodiment, the base 12 is a glass plate. The base 12, which is formed of a translucent material such as a glass plate, has an advantage in that each workplace in the cell movement line 20 arranged on a top surface of the base 12 can be imaged by the camera unit 50 arranged below the base 12 through the base 12. Note that a sheet metal plate in which only a region necessary for the imaging is a glass window may be used as the base 12.

An upper frame 13, which is a flat plate elongated in the left-right direction, and an intermediate frame 14, which is also a flat plate elongated in the left-right direction and is arranged below the upper frame 13 with a gap therebetween, are arranged above the base 12. The frames 13 and 14 are held by a frame stand (not shown) vertically arranged on the base 12. A pair of upper guide rails 131 for moving the head unit 30 along the left-right direction are laid on a top surface of the upper frame 13. A pair of intermediate guide rails 141 for moving the illumination unit 40 along the left-right direction are laid on a top surface of the intermediate frame 14. Further, a lower frame 15, which is a flat plate elongated in the left-right direction, is arranged below the base 12. Right and left end portions of the lower frame 15 are held by the side frames 112. A pair of lower guide rails 151 for moving the camera unit 50 in the left-right direction are laid on a top surface of the lower frame 15.

The cell movement line 20 includes a plurality of workplaces necessary for implementation of a series of cell movement steps for extracting a desired cell aggregate from a cell-containing liquid and moving the extracted cell aggregate to a predetermined container. The workplaces are incorporated into the base 12 side by side in the left-right direction (first direction). The cell movement line 20 includes, as the plurality of workplaces, an object stock portion 21 configured to store a cell-containing liquid, a dispenser tip stock portion 22, a cell sorting portion 23 (first container) configured to store a cell-containing liquid (cell culture liquid) dispensed for sorting of cell aggregates, a tip stock portion 24, a tip imaging portion 25, a cell transfer portion 26 (second container) configured to receive a sorted cell aggregate, a black cover placement portion 27, and a tip discarding portion 28. Details of each of the portions are described later.

Figure 8:
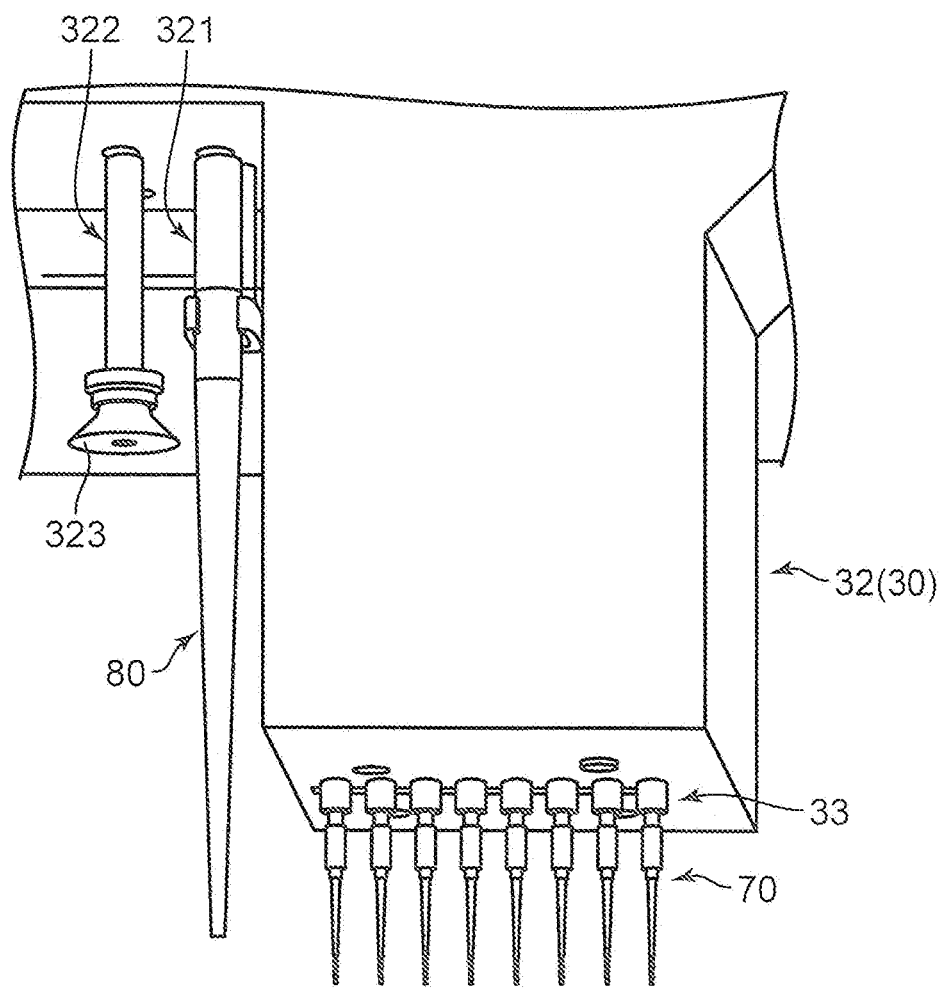
FIG. 8 is a main perspective view of the head unit.

The head unit 30 includes a unit main body 31 and a head portion 32. FIG. 8 is a perspective view of the head portion 32. The head portion 32 includes a plurality of heads 33, a first nozzle 321, and a second nozzle 322, each of which is movable in the up-down direction. Each head 33 includes a rod 331 (see FIG. 9) vertically movable, and protrudes from a lower end surface of a housing of the head portion 32. A cylinder tip 70 configured to suck and discharge a cell aggregate is mounted to the head 33. This embodiment indicates an example in which eight heads 33 are arranged in line in the left-right direction. The number of the heads 33 is freely selected, and the heads 33 may be arranged in a matrix in the X-Y direction.

The first nozzle 321 and the second nozzle 322 are nozzles capable of generating a suction airflow and a discharge airflow, and are each provided with an opening portion at a lower end thereof. A piston mechanism (described later) for generating a suction force and a discharge force at the opening portion is provided inside each of the first nozzle 321 and the second nozzle 322. A head drive device 17 (see FIG. 13) including a mechanism for vertically moving the head 33, the first nozzle 321, and the second nozzle 322 and a mechanism for operating the rod 331 and the piston mechanism is built in the unit main body 31.

The head unit drive device 30M includes a first X slider device 30X for moving the head unit 30 in the left-right direction and a first Y slider device 30Y for moving the head unit 30 in the front-back direction. The first X slider device 30X includes a first X ball screw device 34 and a first X slider 35 to be moved in the left-right direction by the first X ball screw device 34. The first X ball screw device 34 includes a first X motor 341 (see FIG. 19), a first X screw shaft 342, and a first X nut member 343. The first X motor 341 is a motor configured to generate a rotary drive force for rotating the first X screw shaft 342 about its axis in the forward and reverse directions. The first X screw shaft 342 extends in the left-right direction, and a circumferential surface thereof is threaded with a male screw. The first X nut member 343 has a female screw on an inner surface thereof, and is engaged with the first X screw shaft 342. When the first X screw shaft 342 rotates in the forward or reverse direction, the first X nut member 343 moves rightward or leftward.

The first X slider 35 is a flat plate-shaped member configured to hold the first Y slider device 30Y and the head unit 30. Guided portions 352 to be fitted into the pair of upper guide rails 131 are provided on a lower surface of the first X slider 35. Although the illustration of the first X slider 35 is omitted in FIG. 2, the first X slider 35 is fixed to the first X nut member 343. Thus, when the first X motor 341 operates, the first X slider 35 can move in the left-right direction while being guided by the upper guide rails 131.

The first Y slider device 30Y includes a first Y ball screw device 36, a first Y slider 37 to be moved in the front-back direction by the first Y ball screw device 36, and a slider arm 38 (slider) mounted to the first Y slider 37. The first Y ball screw device 36 includes a first Y motor 361, a first Y screw shaft 362, and a first Y nut member 363. The first Y motor 361 is a motor configured to generate a rotary drive force for rotating the first Y screw shaft 362 about its axis in the forward and reverse directions. The first Y screw shaft 362 extends in the front-back direction, and a circumferential surface thereof is threaded with a male screw. The first Y nut member 363 has a female screw on an inner surface thereof, and is engaged with the first Y screw shaft 362. When the first Y screw shaft 362 rotates in the forward or reverse direction, the first Y nut member 363 moves frontward or backward.

The first Y slider 37 is fixed to the first Y nut member 363. Guided portions 371 to be fitted into a guide rail 351, which is laid on a top surface of the first X slider 35 and extends in the front-back direction, are mounted on a lower surface of the first Y slider 37. Thus, when the first Y motor 361 operates, the first Y slider 37 can move in the front-back direction while being guided by the guide rail 351. The slider arm 38 is a housing-shaped member that is elongated in the front-back direction and is rectangular in cross section. The slider arm 38 is mounted to a top surface of the first Y slider 37. The slider arm 38 reciprocates in the front-back direction along with the movement of the first Y slider 37 in the front-back direction. The head unit 30 is mounted to a front end (distal end) of the slider arm 38.

In the slider arm 38, power supply cables and control cables for electric devices included in the head unit 30 are wired. Part of the cables that extend from the slider arm 38 are protected by a cable protection member 36C and a cable protection member 35C. The cable protection member 36C is bent into a U-shape convex rearward and follows the movement of the first Y slider 37. The cable protection member 35C is bent into a U-shape convex leftward and follows the movement of the first X slider 35.

Figure 17:
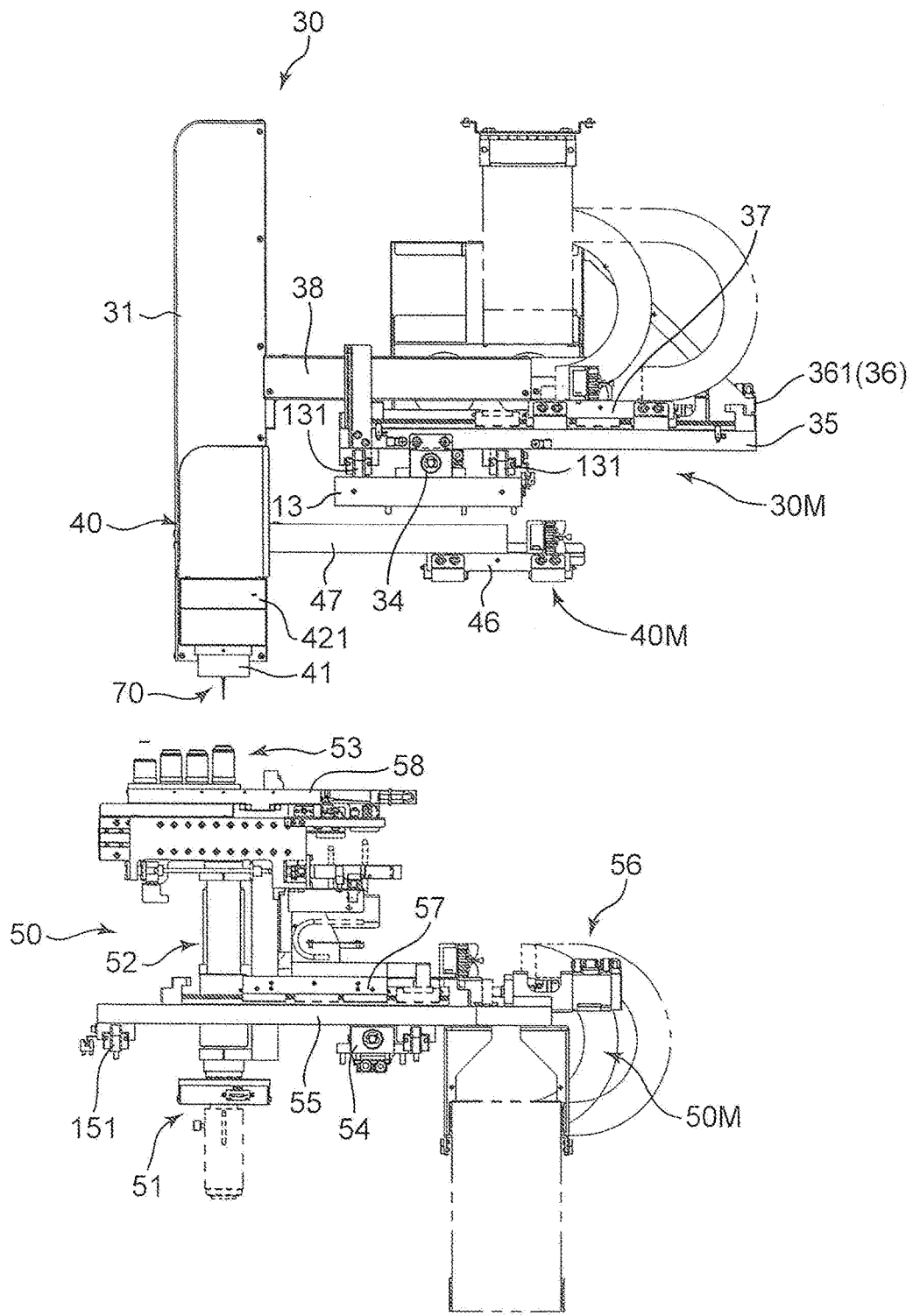
FIG. 17 is a side view of the head unit, the illumination unit, and the camera unit as viewed from the +X direction in a state in which the work step in FIG. 16 is executed.

The head unit drive device 30M having the configuration described above enables the head unit 30 mounted to the front end of the slider arm 38 to freely move in the left-right direction and the front-back direction. Consequently, the head unit 30 (head portion 32) can move above the base 12 along a predetermined movement path on the cell movement line 20. Note that FIG. 2 illustrates the state in which the slider arm 38 retreats backward and FIG. 3 illustrates the state in which the slider arm 38 advances frontward (FIG. 17 is a side view corresponding to the state in FIG. 2).

The illumination unit 40 is arranged so as to be movable above the base 12 in the left-right direction and the front-back direction in order to illuminate mainly the cell sorting portion 23 and the cell transfer portion 26 from above. The illumination is used as transmitted illumination for imaging a cell aggregate held in the cell sorting portion 23 or the cell transfer portion 26 with the camera unit 50. The illumination unit 40 includes an illumination head 41 (light source) configured to emit illumination light and an illumination unit main body portion 42.

The illumination unit main body portion 42 includes a halogen lamp serving as a light source and optical components such as a collector lens, a ring slit, an aperture stop, an optical filter, and a condenser lens, which are arranged in the up-down direction. In the illumination head 41, the optical component closest to the image plane side (condenser lens) is arranged. Note that a tungsten lamp, a mercury lamp, a xenon lamp, a light emitting diode (LED), or the like may be used as the light source instead of the halogen lamp. A protruding portion 421 that protrudes in the left-right direction is provided in the vicinity of a lower end of the illumination unit main body portion 42. The position of the protruding portion 421 is a height position at which the optical filter is arranged. The illumination unit 40 in this embodiment is provided with a plurality of (three) types of optical filters for fluorescent observation of cell aggregates. The protruding portion 421 is a portion that provides a space for retreating an unused filter from the optical path when an optical filter is switched to another one.

The illumination unit drive device 40M includes a second X slider device 40X for moving the illumination unit 40 in the left-right direction and a second Y slider device 40Y for slightly moving the illumination unit 40 in the front-back direction. The second X slider device 40X includes a second X ball screw device 43 and a second X slider 44 to be moved in the left-right direction by the second X ball screw device 43. The second X ball screw device 43 includes a second X motor 431, a second X screw shaft 432, and a second X nut member 433. The second X motor 431 is a motor configured to generate a rotary drive force for rotating the second X screw shaft 432 about its axis in the forward and reverse directions. The second X screw shaft 432 is a screw shaft extending in the left-right direction. The second X nut member 433 is engaged with the second X screw shaft 432. When the second X screw shaft 432 rotates in the forward or reverse direction, the second X nut member 433 moves rightward or leftward. Note that the second X nut member 433 is virtually illustrated in FIG. 2 but the second X nut member 433 is fixed to the second X slider 44 in practice.

The second X slider 44 is a flat plate-shaped member configured to hold the second Y slider device 40Y and the illumination unit 40. Guided portions (not shown) to be fitted into the pair of intermediate guide rails 141 are provided on a lower surface of the second X slider 44. Thus, when the second X motor 431 operates, the second X slider 44 can move in the left-right direction while being guided by the intermediate guide rails 141.

The second Y slider device 40Y includes a second Y ball screw device (not shown) and a second Y slider 46 to be moved in the front-back direction for a relatively short distance by the second Y ball screw device. The second Y ball screw device includes a second Y motor (not shown), a second Y screw shaft (not shown) to be driven to rotate by the second Y motor, and a second Y nut member (not shown) configured to move forward or backward when the second Y screw shaft rotates in the forward or reverse direction. The second Y slider 46 is fixed to the second Y nut member.

The second Y slider 46 is provided with guided portions 461 on a lower surface thereof, and is assembled to guide rails arranged on a top surface of the second X slider 44. An illumination arm portion 47 is mounted to a top surface of the second Y slider 46. The illumination arm portion 47 can move in the front-back direction along with the movement of the second Y slider 46 in the front-back direction. The illumination unit 40 is mounted to a front end of the illumination arm portion 47. Consequently, the illumination unit 40 can move above the base 12 in the left-right direction and the front-back direction by the illumination unit drive device 40M.

The illumination unit 40 is arranged between the slider arm 38 and the base 12 in the state in which the slider arm 38 extends frontward as illustrated in FIG. 3. Specifically, a top surface of the illumination unit 40 is located below a bottom surface of the slider arm 38. In the state in which the slider arm 38 retreats backward, the head unit 30 and the illumination unit 40, both of which are arranged above the base 12, have a positional relationship in which the head unit 30 and the illumination unit 40 interfere with each other in the left-right direction (see FIG. 17). In the state in which the slider arm 38 extends frontward, however, the illumination unit 40 and the head unit 30 have a positional relationship in which the illumination unit 40 and the head unit 30 do not interfere with each other. Thus, the head unit 30 can move on a path that bypasses the illumination unit 40 and pass the illumination unit 40 when the head unit 30 moves in the left-right direction.

The camera unit 50 is arranged below the base 12 so as to be movable in the left-right direction and the front-back direction in order to image cell aggregates held in the cell sorting portion 23 and the cell transfer portion 26 from below the base 12. In this embodiment, the camera unit 50 is also used to observe how the cylinder tip 70 is mounted to the head 33 in the tip imaging portion 25. The camera unit 50 includes a camera 51, a condenser lens 52, a switchable objective lens unit 53, and an epi-illumination device (not shown).

The camera 51 includes an image pickup element such as a CCD image sensor, and acquires a still image or a moving image of an object. The condenser lens 52 and the objective lens unit 53 are optical components for forming an optical image of the object on a light receiving surface of the CCD image sensor. The epi-illumination device is arranged on the side of the condenser lens 52. In this embodiment, in the case of imaging the cell aggregate, the camera 51 implements an imaging operation under the state in which illumination light is emitted from the illumination head 41 of the illumination unit 40 (transmitted illumination). In the case of imaging the tip in the tip imaging portion 25, on the other hand, the camera 51 implements an imaging operation under the state in which the epi-illumination device is turned on (or under the state in which an LED illumination device assembled in the tip imaging portion 25 is turned on) (side illumination). Note that a dedicated illumination device for imaging the tip may be mounted in the camera unit 50.

The camera unit drive device 50M includes a third X slider device 50X for moving the camera unit 50 in the left-right direction and a third Y slider device 50Y for slightly moving the camera unit 50 in the front-back direction. The third X slider device 50X includes a third X ball screw device 54 and a third X slider 55 to be moved in the left-right direction by the third X ball screw device 54. The third X ball screw device 54 includes a third X motor 541, a third X screw shaft 542, and a third X nut member 543. The third X motor 541 is a motor configured to generate a rotary drive force for rotating the third X screw shaft 542 about its axis in the forward and reverse directions. The third X screw shaft 542 is a screw shaft extending in the left-right direction. The third X nut member 543 is engaged with the third X screw shaft 542. When the third X screw shaft 542 rotates in the forward or reverse direction, the third X nut member 543 moves rightward or leftward. Note that the third X nut member 543 is virtually illustrated in FIG. 2 but the third X nut member 543 is fixed to the third X slider 55 in practice.

The third X slider 55 is a flat plate-shaped member configured to hold the third Y slider device 50Y and the camera unit 50. Guided portions 551 to be fitted into the pair of lower guide rails 151 are provided on a lower surface of the third X slider 55. Thus, when the third X motor 541 operates, the third X slider 55 can move in the left-right direction while being guided by the lower guide rails 151.

The third Y slider device 50Y includes a third Y ball screw device 56 and a third Y slider 57 configured to move a camera field of view area in the front-back direction for a desired distance by the third Y ball screw device 56. The third Y ball screw device 56 includes a third Y motor 561, a third Y screw shaft 562 to be driven to rotate by the third Y motor 561, and a third Y nut member (not shown) configured to move forward or backward when the third Y screw shaft 562 rotates in the forward or reverse direction. The third Y slider 57 is fixed to the third Y nut member. Note that the objective lens unit 53 is mounted on a fourth Y slider 58 that is freely movable in the front-back direction relative to a frame of the camera unit 50, thereby enabling one objective lens to be arranged on the optical axis.

The third Y slider 57 is assembled to guide rails arranged on a top surface of the third X slider 55. When the third Y motor 561 operates, the third Y slider 57 can move in the front-back direction along the guide rails. The camera unit 50 is mounted on the third Y slider 57. Thus, the camera unit 50 can move below the base 12 in the left-right direction and the front-back direction by the camera unit drive device 50M.

Figure 4:
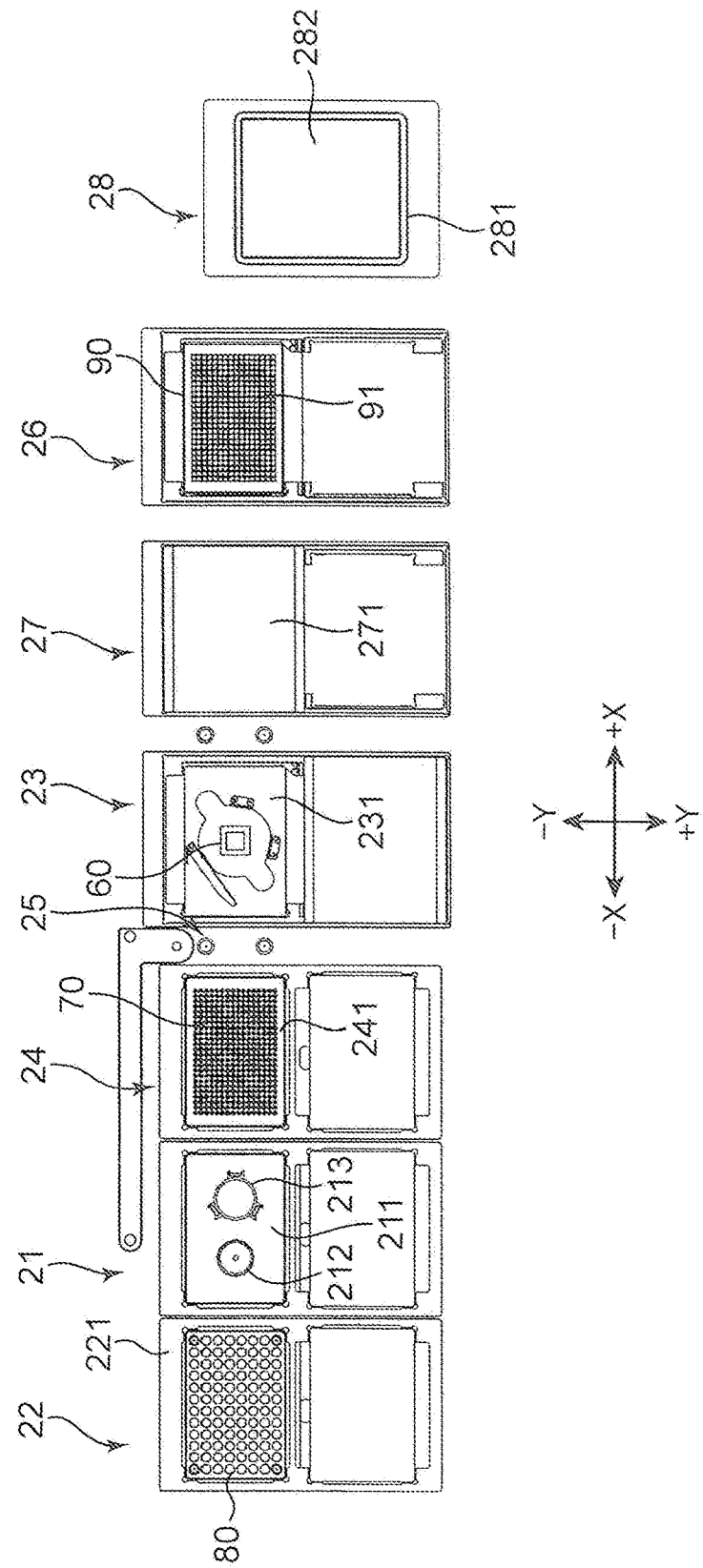
FIG. 4 is a top plan view of a movement line.

Subsequently, the details of the cell movement line 20 are described. FIG. 4 is a top plan view of the cell movement line 20. In the cell movement line 20, the dispenser tip stock portion 22, the object stock portion 21, the tip stock portion 24, the tip imaging portion 25, the cell sorting portion 23, the black cover placement portion 27, the cell transfer portion 26, and the tip discarding portion 28 are arranged in line in the left-right direction (first direction) in this order from the left end side in FIG. 4. The arrangement in the cell movement line 20 illustrated in FIG. 4 is merely an example, and the arrangement positions of the portions can be appropriately set in consideration of work efficiency and the like. For example, the black cover placement portion 27 may be arranged on the front side (+Y) or the back side (−Y) of the cell sorting portion 23 and the cell transfer portion 26.

The object stock portion 21 is a site where a cell culture liquid dispersed with a large amount of cell aggregates (moving objects) as a dispensing source is stored. The object stock portion 21 includes a box 211, a tube 212 held in the box 211, and a lid member 213 placed on the box 211. The box 211 holds the tube 212 in a state in which an upper end of the tube 212 protrudes from the box 211. The box 211 is assembled to the base 12 in a manner that an upper edge of the box 211 is fitted into a rectangular opening provided in the base 12. The tube 212 is a cylindrical container whose upper surface is opened, and stores a cell culture liquid containing cell aggregates and impurities. The lid member 213 is a member for closing the opening in the tube 212. In a period during which a dispensing work is not executed, the lid member 213 is put on the opening portion in the tube 212 in order to prevent entry of dust or the like into the tube 212. The movement of the lid member 213 is implemented by an adsorption and adsorption-release operation of the lid member 213 by a sucking disk head 323 (FIG. 8) mounted to the second nozzle 322 and a movement operation of the head portion 32.

Figure 11:
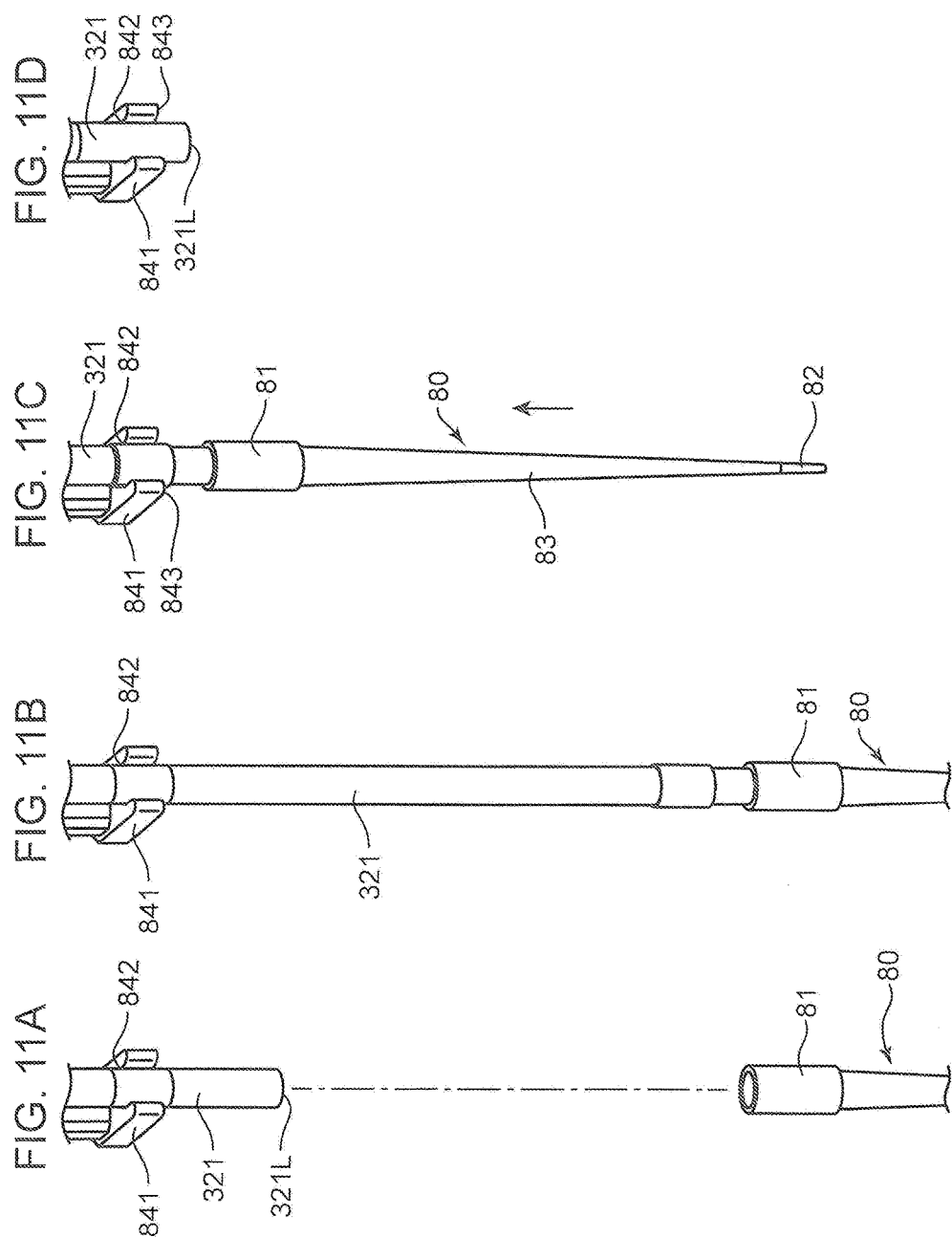
FIGS. 11A to 11D are perspective views for describing an operation of mounting and removing a dispenser tip to a nozzle included in the head portion.

The dispenser tip stock portion 22 is a site where a plurality of dispenser tips 80 are stored. Referring to FIG. 8 and FIG. 11C, the dispenser tip 80 is an elongated tube-shaped member, and includes an upper end portion 81 to be fitted to the first nozzle 321, a lower end portion 82 that has an opening formed at an edge thereof for sucking and discharging a cell culture liquid, and an intermediate portion 83 extending between the upper end portion 81 and the lower end portion 82. The intermediate portion 83 has a tapered shape in which the outer diameter is gradually reduced from the upper end portion 81 side to the lower end portion 82 side. The dispenser tip 80 is mountable and removable to and from the first nozzle 321. As described above, the first nozzle 321 is a nozzle capable of generating a suction force and a discharge force, and the dispenser tip 80 sucks a cell culture liquid when applied with the suction force and discharges the sucked cell culture liquid when applied with the discharge force.

The dispenser tip stock portion 22 includes a holding box 221 configured to hold the dispenser tips 80 that are arranged in a matrix in a standing manner. The dispenser tip 80 is held in the holding box 221 in a state in which the upper end portion 81 of the dispenser tip 80 protrudes upward from an upper end surface of the holding box 221. Specifically, the dispenser tip 80 is held in the holding box 221 in a state in which the dispenser tip 80 is easily mountable to the first nozzle 321 moving in the up-down direction.

The cell sorting portion 23 is arranged at a center position of the cell movement line 20 in the left-right direction, and is a site for sorting a desired size of a cell aggregate from a cell culture liquid containing various sizes of cell aggregates and impurities. The cell sorting portion 23 includes a dish 60 (first container) and a holding table 231. The dish 60 is an upper surface-opened container into which a cell culture liquid containing cell aggregates is poured by the dispenser tip 80 and which is capable of storing the cell culture liquid. The holding table 231 is a transparent member which is placed on the base 12 and configured to hold the dish 60 in a positioned manner.

Figure 5:
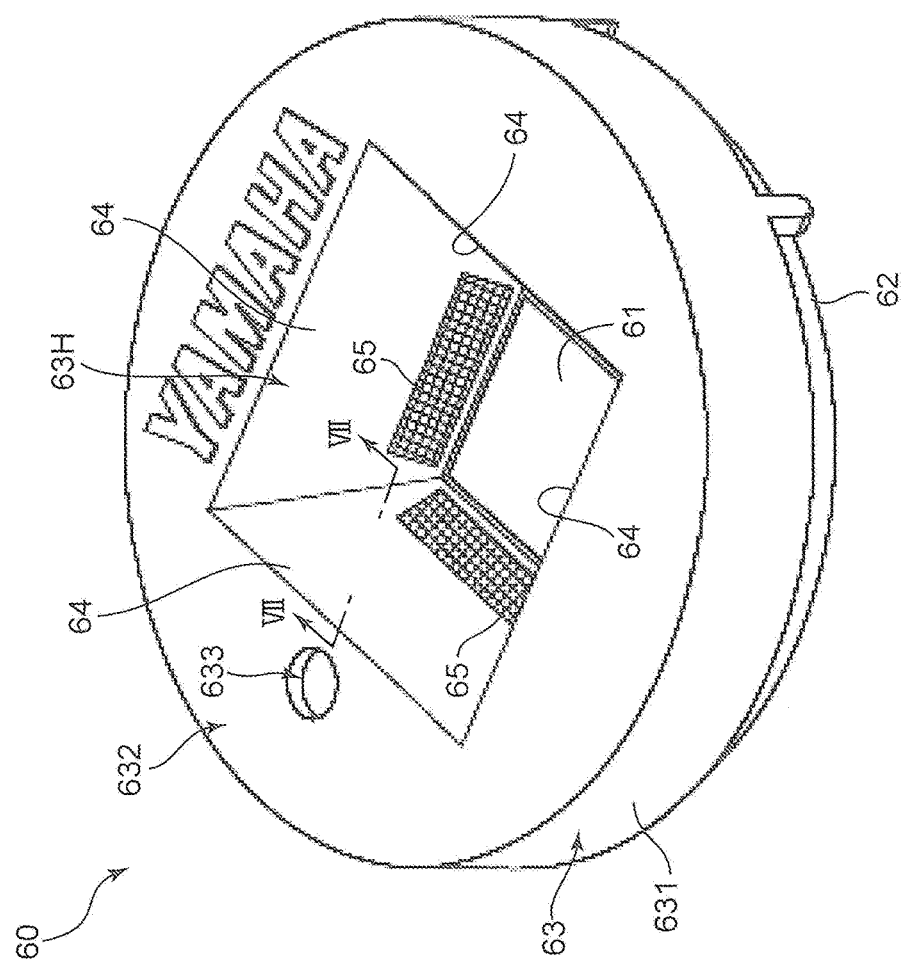
FIG. 5 is a perspective view of a dish to which a liquid containing a cell aggregate as a moving object is dispensed.

FIG. 5 is a perspective view of the dish 60. The dish 60 includes a well plate 61, a Petri dish (Schale) 62, and a cover member 63. The well plate 61 is a plate that is square in top view and used to carry a predetermined size of a cell aggregate. The Petri dish 62 is a flat, shallow dish with its top surface opened, and is a container for collecting a cell culture liquid containing small cell aggregates other than those of desired sizes and impurities. The well plate 61 is held in the vicinity of a central bottom surface of the Petri dish 62. The cover member 63 is a bottom surface-opened member that includes a cylinder portion 631 having an inner diameter larger than the outer diameter of the Petri dish 62, and a disk-shaped lid portion 632 closing an upper end of the cylinder portion 631. The cover member 63 is fitted on the Petri dish 62 so that the lid portion 632 covers the upper opening in the Petri dish 62. A through hole 633 is formed in the lid portion 632. Through the through hole 633, a cell culture liquid can be poured into a cavity in the Petri dish 62 or be sucked from the Petri dish 62. In this embodiment, the dish 60 is formed by a translucent member, such as transparent plastic and transparent glass.

An opening 63H is provided at the center of the lid portion 632. The opening 63H is a square opening larger than the well plate 61. The cover member 63 includes four trapezoidal inclined plates 64, which extend from the four sides defining the opening 63H toward the cylindrical center of the dish 60 and each of which is inclined downward. Each lower edge of the inclined plates 64 is located in the vicinity of each side of the well plate 61. A belt-shaped mesh opening portion 65 is provided in the vicinity of a lower end of each inclined plate 64. The mesh opening portion 65 is formed of a plurality of holes passing through the inclined plate 64. The mesh opening portions 65 communicate the cavity in the Petri dish 62 and an internal space defined by the four inclined plates 64 to each other. The mesh size of the mesh opening portion 65 is selected so as to prevent a desired size of a cell aggregate from passing therethrough and allow small cell aggregates other than those of desired sizes and impurities to pass therethrough.

Figure 6:
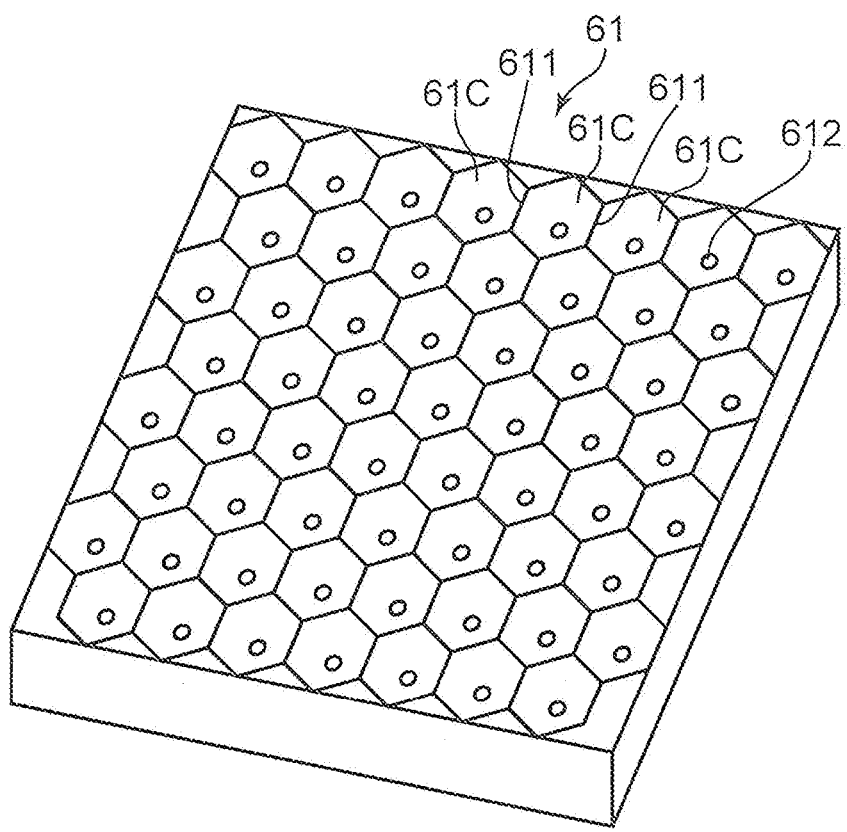
FIG. 6 is a perspective view of a well plate provided to the dish.
Figure 7:
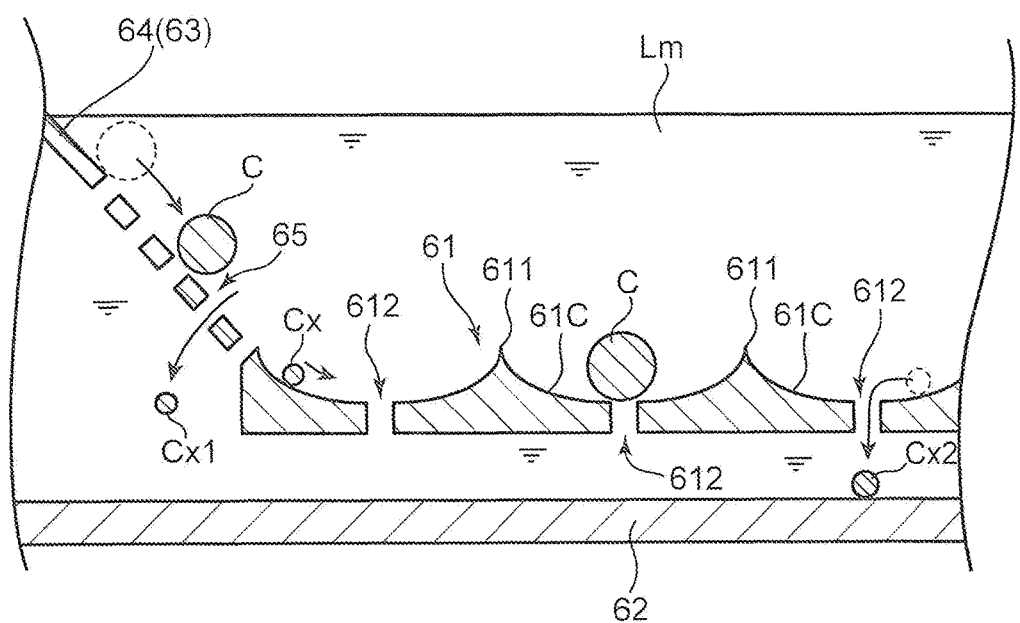
FIG. 7 is a cross-sectional view for describing a cell sorting operation in the dish.

FIG. 6 is a perspective view of the well plate 61. FIG. 7 is a cross-sectional view taken along the line VII-VII in FIG. 5, for describing the cell sorting operation in the dish 60. The well plate 61 includes, on the top surface side, a plurality of recesses 61C for carrying cell aggregates. Each recess 61C has a semispherical cavity, and an upper end opening edge 611 thereof is hexagonal. The plurality of recesses 61C are arranged in a honeycomb pattern in a manner that the upper end opening edges 611 of the recesses 61C are adjacent to each other. In another embodiment, the shape of the upper end opening edge 611 of the recess 61C is a polygon other than a hexagon, for example, a rectangle. As illustrated in FIG. 7, the curvature of radius of the recess 61C is relatively small in the vicinity of the bottom part, and relatively large in the vicinity of the upper end opening edge 611. Thus, a ridge part formed by upper end opening edges 611 of adjacent recesses 61C in contact with each other is formed by a sharp, convex distal end part.

In each recess 61C, a release hole 612 passing through the well plate 61 in the up-down direction is formed. The release hole 612 is arranged at the center part (deepest part) of the recess 61C. The size of the release hole 612 is selected so as to prevent a desired size of a cell aggregate from passing therethrough and allow small cell aggregates other than those of desired sizes and impurities to pass therethrough. Each recess 61C is intended to house one cell aggregate. A gap with a predetermined height is provided between a rear surface of the well plate 61 and an inner bottom surface of the Petri dish 62.

For implementing the cell sorting operation, a cell culture liquid Lm containing no cell aggregate C is first poured into the Petri dish 62 through the through hole 633, for example. As illustrated in FIG. 7, the liquid level of the cell culture liquid Lm is set so that the well plate 61 and the mesh opening portion 65 of the inclined plate 64 are immersed. After that, a cell culture liquid containing a cell aggregate C to be extracted and impurities Cx, which are inevitably mixed therein, is poured through the opening 63H in the lid portion 632. Then, the cell aggregate C with a desired size cannot pass through the mesh opening portion 65, and thus, is guided onto the well plate 61. On the other hand, the impurities Cx pass through the mesh opening portion 65 and are collected in the Petri dish 62 (Cx1). Even if the impurities Cx are not trapped by the mesh opening portion 65 but enter the recess 61C in the well plate 61, the impurities Cx drop through the release hole 612 to be collected in the Petri dish 62 (Cx2).

Sorting of the cell aggregate C and the impurities Cx is implemented as described above, and hence only the cell aggregate C is left on the well plate 61. Note that a plurality of cell aggregates C may be carried in one recess 61C. If this is problematic, it is desired that the holding table 231 be provided with a mechanism configured to vibrate the well plate 61. Through application of horizontal vibration to the holding table 231 in the X direction and the Y direction, one cell aggregate C that is carried in one recess 61C together with another cell aggregate C in an overlapped manner can be easily moved to another recess 61C. The shape of the recess 61C in which the curved surface in the vicinity of the bottom part is gentle close to a flat surface, while the surface in the vicinity of the upper end opening edge 611 is relatively steeply curved, contributes to the moving effect. As described above, the dish 60 is formed of a transparent member and the base 12 is also translucent, and hence an image of the cell aggregate C carried in the recess 61C can be taken by the camera 51 under illumination of the illumination head 41.

The tip stock portion 24 is arranged on the left of the cell sorting portion 23, and is a site where a plurality of cylinder tips 70 (one example of tip) are held. The cylinder tip 70 is an elongated tubular member as illustrated in FIG. 8, and is mountable and removable to and from the head 33. The cylinder tip 70 functions to suck a cell aggregate carried in the recess 61C of the well plate 61, transport the cell aggregate along with the movement of the head unit 30, and discharge the cell aggregate to the cell transfer portion 26.

The tip stock portion 24 includes a holding box 241 configured to hold the cylinder tips 70 that are arranged in a matrix in a standing manner. The cylinder tip 70 is held in the holding box 241 in a state in which an upper end part of the cylinder tip 70 protrudes from an upper end surface of the holding box 241. Specifically, the cylinder tip 70 is held in the holding box 241 in a state in which the cylinder tip 70 is easily mountable to the head 33 moving in the up-down direction.

Figure 9:
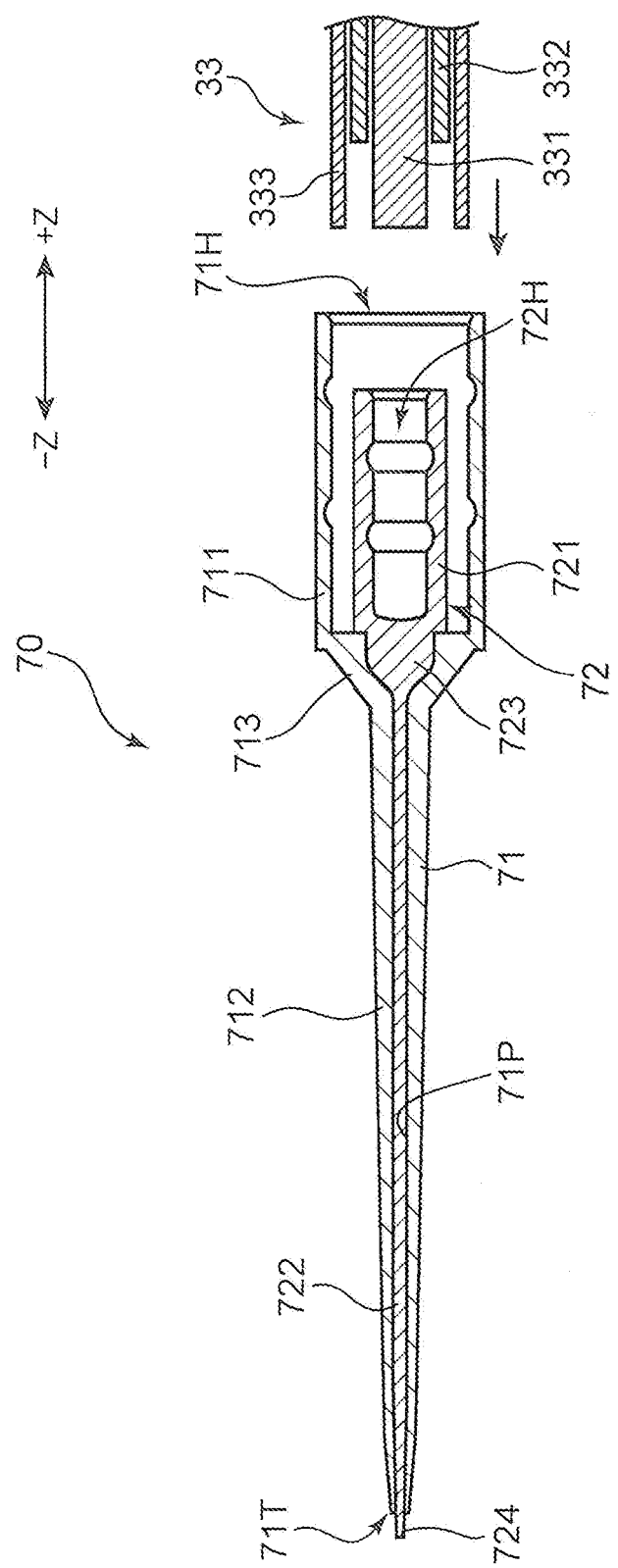
FIG. 9 is a cross-sectional view of a cylinder tip.

FIG. 9 is a cross-sectional view illustrating the internal structure of the cylinder tip 70 and the head 33. The cylinder tip 70 includes a syringe 71 having a tubular passage 71P inside, which serves as a suction path for sucking a cell aggregate, and a plunger 72 configured to reciprocate in the tubular passage 71P while sliding in contact with an inner circumferential wall of the syringe 71 that defines the tubular passage 71P. The syringe 71 includes a syringe base end portion 711 formed of a cylindrical body having a large diameter, a syringe main body portion 712 formed of an elongated cylindrical body having a small diameter, and a tapered cylinder portion 713 connecting the base end portion 711 and the main body portion 712 to each other. The tubular passage 71P is formed in the syringe main body portion 712. A suction port 71T (serving also as a discharge port) is provided in a distal end of the syringe main body portion 712. The plunger 72 includes a plunger base end portion 721 formed of a cylindrical body, a needle-shaped plunger main body portion 722, and a hemisphere portion 723 connecting the base end portion 721 and the main body portion 722 to each other.

The syringe base end portion 711 has a cylindrical hollow portion 71H. The outer diameter of the plunger base end portion 721 is set to be smaller than the inner diameter of the hollow portion 71H by a predetermined length. The outer diameter of the plunger main body portion 722 is set to be slightly smaller than the inner diameter of the tubular passage 71P. Further, the shape of an inner circumferential surface of the tapered cylinder portion 713 conforms to the curved surface shape of an outer circumferential surface of the hemisphere portion 723. The plunger 72 is assembled to the syringe 71 in a manner that the plunger base end portion 721 is housed in the hollow portion 71H and the plunger main body portion 722 is inserted into the tubular passage 71P in the syringe main body portion 712.

FIG. 9 illustrates the state in which the plunger main body portion 722 is inserted into the syringe main body portion 712 most deeply, that is, the state in which the plunger 72 is lowered most. In this case, the hemisphere portion 723 is completely received in a cavity in the tapered cylinder portion 713. The length of the plunger main body portion 722 is slightly larger than the length of the syringe main body portion 712. In the state in FIG. 9, the distal end portion 724 protrudes from the suction port 71T. Further, a gap exists between an inner circumferential surface of the syringe base end portion 711 and an outer circumferential surface of the plunger base end portion 721.

The plunger 72 can move in the up direction (+Z) with respect to the syringe 71 from the state in FIG. 9. When the plunger 72 moves in the up direction by a predetermined length, the distal end portion 724 of the plunger main body portion 722 sinks in the tubular passage 71P. In this case, a suction force can be generated from the suction port 71T to suck a liquid (in this embodiment, a cell culture liquid) around the suction port 71T into the tubular passage 71P. After the suction, when the plunger 72 is moved downward, the liquid sucked into the tubular passage 71P can be discharged from the suction port 71T.

The head 33 includes a columnar rod 331 that is movable in the up-down direction, a cylindrical movable cylinder 332 that is arranged around the rod 331 and movable in the up-down direction, and a cylindrical fixed cylinder 333 that is arranged around the movable cylinder 332. Further, the head 33 can move in the Z direction as a whole.

A mounting hole 72H formed of a cylindrical hollow space, which has an opening at an end surface thereof in the up direction, is provided in the plunger base end portion 721. This mounting hole 72H is a hole for press-fitting a distal end of the rod 331 therein, and the press-fitting enables the rod 331 and the plunger 72 to be moved integrally in the up-down direction. The movable cylinder 332 is movable in the up-down direction independently from the rod 331. A lower end surface of the movable cylinder 332 is opposed to an upper end surface of the plunger base end portion 721. The fixed cylinder 333 is a cylinder to which the syringe base end portion 711 is press-fitted. When press-fitted, the fixed cylinder 333 enters the gap between the syringe base end portion 711 and the plunger base end portion 721.

Subsequently, the suction and discharge operation for a cell aggregate C by the cylinder tip 70 is described with reference to FIGS. 10A to 10E. A case is described in which the cylinder tip 70 is used to suck a cell aggregate C present in a cell culture liquid Lm1 stored in a container C1 and discharge the cell aggregate C into a cell culture liquid Lm2 stored in a container C2. In the case of this embodiment, the container C1 corresponds to the cell sorting portion 23 and the container C2 corresponds to each container arranged in the cell transfer portion 26.

Figure 10:
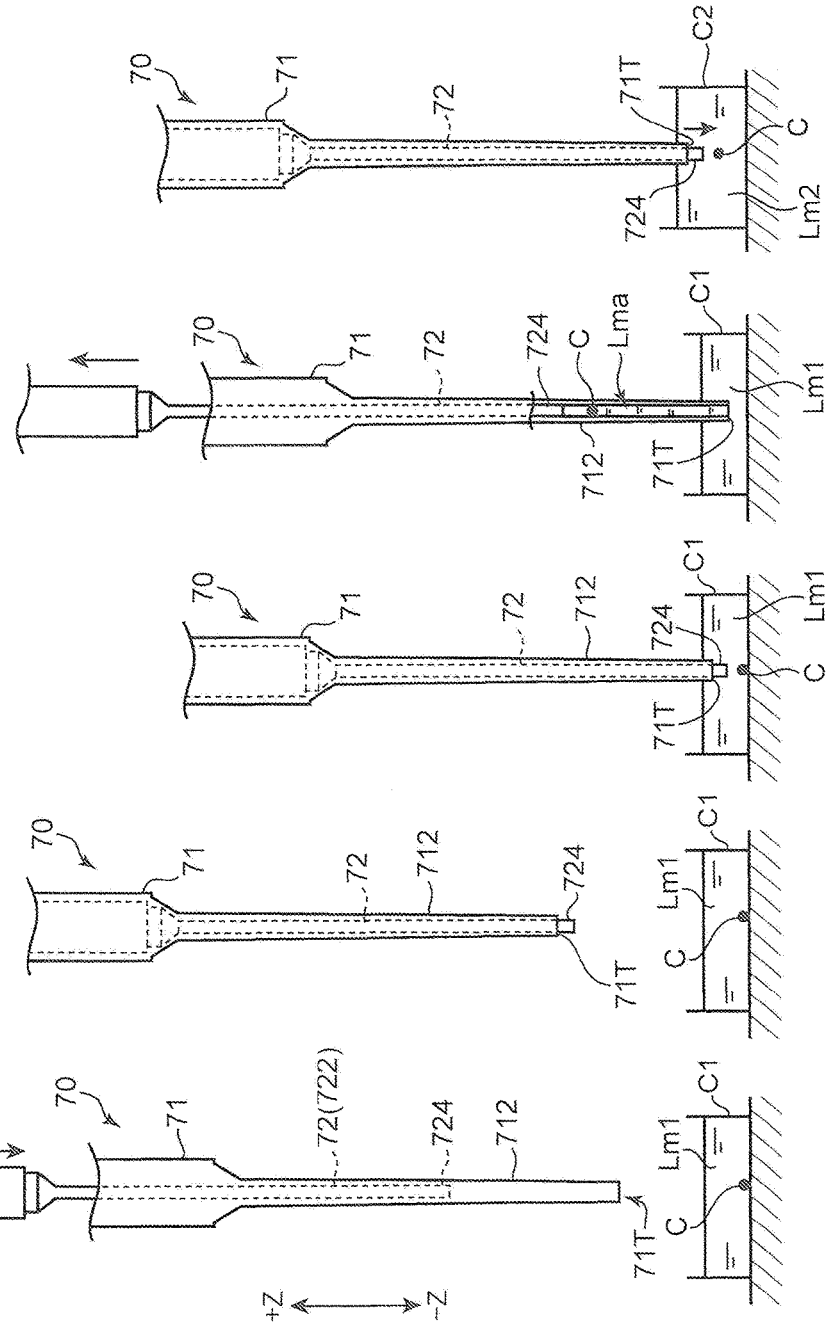
FIGS. 10A to 10E are schematic diagrams illustrating operations of sucking and discharging a cell aggregate by the cylinder tip.

As illustrated in FIG. 10A, the cylinder tip 70 is moved directly above the cell aggregate C to be sucked. If the plunger 72 has moved upward (+Z) relative to the syringe 71 and the distal end portion 724 of the plunger main body portion 722 has sunk into the syringe main body portion 712, the plunger 72 is moved to the lowest position (-Z) so that the distal end portion 724 protrudes from the suction port 71T as illustrated in FIG. 10B. Specifically, the state in which no air is present in the tubular passage 71P in the syringe main body portion 712 is established. After that, as illustrated in FIG. 10C, the cylinder tip 70 is lowered as a whole so that the suction port 71T enters the cell culture liquid Lm1 in the container C1. In this case, the suction port 71T is made closer to the cell aggregate C as much as possible.

Subsequently, as illustrated in FIG. 10D, the plunger 72 is moved upward by a predetermined height. This operation generates a suction force at the suction port 71T so that the cell aggregate C and part of a cell culture liquid Lma are sucked into the syringe main body portion 712. In this state, the cylinder tip 70 is raised as a whole to be moved to the arrangement position of the container C2. Then, as illustrated in FIG. 10E, the cylinder tip 70 is lowered as a whole until the suction port 71T enters the cell culture liquid Lm2 in the container C2. After that, the plunger 72 at a predetermined height position is lowered until the distal end portion 724 protrudes from the suction port 71T. This lowering operation discharges the cell aggregate C into the cell culture liquid Lm2 in the container C2.

Referring back to FIG. 4, the tip imaging portion 25 is a pit for providing a position at which an image of the cylinder tip 70 having the head 33 mounted thereto is taken. The arrangement position of the tip imaging portion 25 is between the cell sorting portion 23 and the tip stock portion 24. In this embodiment, the imaging is performed by the camera unit 50. Therefore, for the imaging, the camera unit 50 is moved directly below the tip imaging portion 25, and takes an image of each cylinder tip 70 under illumination of the epi-illumination device. XYZ coordinate positions of the suction port 71T in the cylinder tip 70 are determined on the basis of the image of the cylinder tip 70 and focus positional information at the time of the imaging. A correction value is derived on the basis of a difference between the coordinate positions and predetermined reference positions. The correction value is used as a correction value for movement control of the head 33 (head unit 30). Note that, instead of the epi-illumination device, an illumination device such as an LED illumination device may be installed in the tip imaging portion 25 itself so that the imaging is performed under illumination of the illumination device.

The cell transfer portion 26 is arranged in the vicinity of the right end portion in the cell movement line 20, and is a site as a movement destination of the cell aggregate sucked from the dish 60 in the cell sorting portion 23. The cell transfer portion 26 includes a microplate 90 (second container) configured to house a cell aggregate. Note that a container similar to the dish 60 may be provided to the cell transfer portion 26 instead of the microplate 90. The microplate 90 is a plate in which a large number of small wells 91 with upper surfaces opened are arranged in a matrix. The microplate 90 is formed of a translucent member, such as transparent plastic. In general, one cell aggregate is housed in one well 91. Thus, a cell aggregate housed in each well 91 can be imaged by the camera 51. Further, the arrangement pitch of the wells 91 is set to be substantially the same as the arrangement pitch of a group of cylinder tips 70 mounted to the heads 33 arranged in line. Consequently, cell aggregates can be discharged to the wells 91 concurrently from a group of the cylinder tips 70. Note that a designated number of cell aggregates may be housed in one well 91, or a designated amount (total volume or total area) of cell aggregates may be housed in one well 91.

The black cover placement portion 27 is a site where the black cover 271 to cover the cell sorting portion 23 or the cell transfer portion 26 is placed. The black cover 271 is a lower surface-opened box, and is a light shielding member used to image a cell aggregate carried on the dish 60 or the microplate 90 in a light shielded state. The black cover 271 is put on the dish 60 or the microplate 90 so as to cover the dish 60 or the microplate 90, for example, when a fluorescent agent is added to the cell culture liquid for fluorescent observation of the cell aggregate.

The tip discarding portion 28 is a site arranged on the right side in the cell movement line 20, where the used cylinder tip 70 and dispenser tip 80 that have finished the suction and discharge operation are discarded. The tip discarding portion 28 includes a collection box 281 for accommodating the used cylinder tip 70 and used dispenser tip 80. For discarding the used chip, the head portion 32 having the cylinder tip 70 or the dispenser tip 80 mounted thereto is moved above the opening portion 282 in the collection box 281, and the operation of removing the cylinder tip 70 or the dispenser tip 80 from the head portion 32 is executed. Through the removal operation, the cylinder tip 70 or the dispenser tip 80 drops in the collection box 281 through the opening portion 282.

The operation of mounting and removing the cylinder tip 70 to and from the head 33 is now described. For mounting the cylinder tip 70 to the head 33, the head portion 32 is moved above the tip stock portion 24, and one head 33 positioned with one cylinder tip 70 is lowered. In this case, as illustrated in FIG. 9, the lower end surface of the rod 331 and the lower end surface of the fixed cylinder 333 are set to be substantially flush with each other, while the lower end surface of the movable cylinder 332 sinks upward with respect to the lower end surfaces. When the head in this state is lowered, the rod 331 is press-fitted into the mounting hole 72H in the plunger base end portion 721, and the fixed cylinder 333 is press-fitted into the hollow portion 71H in the syringe base end portion 711. In this manner, the mounting of the cylinder tip 70 to the head 33 is completed. Simply by vertically moving the rod 331 in this state, the plunger 72 can be reciprocated with respect to the syringe 71.

For removing the cylinder tip 70 from the head 33, the movable cylinder 332 that has been retreated upward (state in FIG. 9) is lowered. Accordingly, the plunger base end portion 721 is pressed downward by the lower end surface of the movable cylinder 332, and the plunger base end portion 721 starts to be removed from the rod 331. Then, the hemisphere portion 723 of the plunger 72 starts to press the inner circumferential surface of the tapered cylinder portion 713 of the syringe 71, and the pressing force of removing the fixed cylinder 333 acts on the syringe 71 as well. When the movable cylinder 332 is lowered more, the cylinder tip 70 finally falls off the head 33.

Next, FIGS. 11A to 11D are perspective view for describing the operation of mounting and removing the dispenser tip 80 to and from the first nozzle 321. A guide arm 841 is attached to the first nozzle 321. The guide arm 841 includes a guide recess 842 that is opened to the side and has an opening width slightly larger than the outer diameter of the first nozzle 321. The first nozzle 321 moves in the up-down direction while being housed in the cavity in the guide recess 842.

For mounting the dispenser tip 80, as illustrated in FIG. 11A, the head portion 32 is moved above the dispenser tip stock portion 22, and the first nozzle 321 positioned with one dispenser tip 80 is lowered. When the first nozzle 321 is lowered, as illustrated in FIG. 11B, a lower end 321L of the first nozzle 321 is fitted into the upper end portion 81 of the dispenser tip 80 so that the first nozzle 321 and the dispenser tip 80 are substantially coupled to each other. Specifically, the cylinder space in the first nozzle 321 and the tubular internal space in the dispenser tip 80 are tightly coupled to each other. Thus, when the first nozzle 321 generates a suction force, a liquid can be sucked from the opening in the lower end portion 82 of the dispenser tip 80. When the first nozzle 321 generates a discharge force, on the other hand, the sucked liquid can be discharged from the opening in the lower end portion 82.

For removing the dispenser tip 80, as illustrated in FIG. 11C, the first nozzle 321 having the dispenser tip 80 mounted thereto is pulled upward. When the first nozzle 321 is pulled up to some extent, the lower end surface 843 of the guide arm 841 and the upper edge of the dispenser tip 80 interfere with each other. As a result of the interference, the dispenser tip 80 is gradually removed from the first nozzle 321, and the dispenser tip 80 finally falls off the first nozzle 321.

Figure 12:
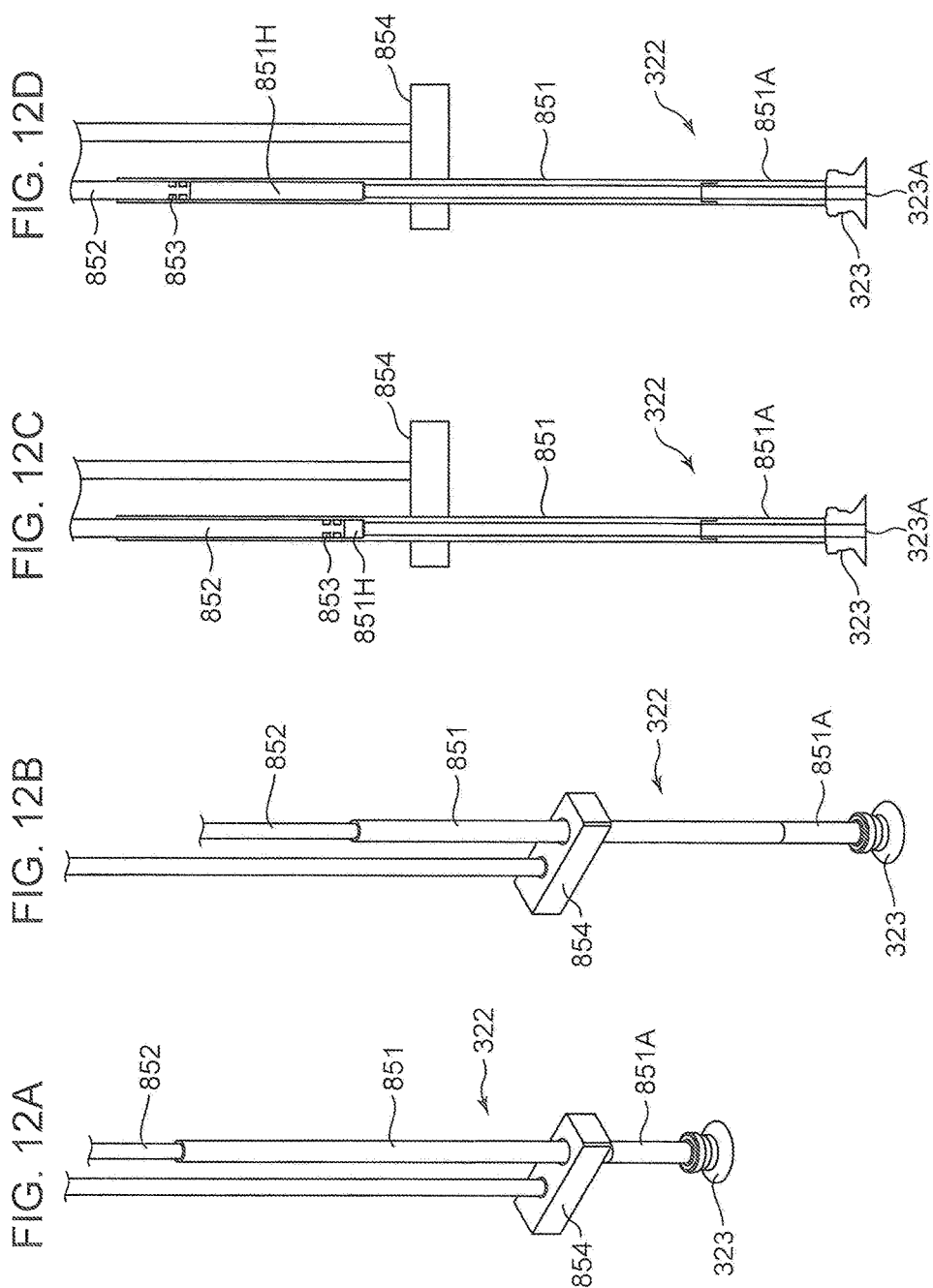
FIGS. 12A and 12B are perspective views of a sucking disk head.
FIGS. 12C and 12D are cross-sectional views of the sucking disk head.

FIGS. 12A and 12B are perspective views of the second nozzle 322 and the sucking disk head 323, and FIGS. 12C and 12D are cross-sectional views thereof. The second nozzle 322 includes a syringe pipe 851, and a piston rod 852 that is housed in the syringe pipe 851 and configured to reciprocate in the up-down direction. The syringe pipe 851 is a straight cylindrical body. A removable coupler pipe 851A is attached to a lower end of the syringe pipe 851. A cylinder space 851H for receiving a lower end part of the piston rod 852 is formed inside an upper end of the syringe pipe 851. A seal member 853 is attached to a lower end of the piston rod 852. The sucking disk head 323 is mounted to the coupler pipe 851A so as to close a lower end opening in the coupler pipe 851A. Note that a suction port 323A is provided at a center part of the sucking disk head 323, and an internal space in the syringe pipe 851 communicates to the outside through the suction port 323A.

The second nozzle 322 can vertically move as a whole while being guided by the guide members 854. Further, the piston rod 852 can vertically move independently. Along with the vertical movement of the piston rod 852, a lower end part of the piston rod 852 provided with the seal member 853 vertically moves in the cylinder space 851H. Along with this vertical movement, a suction force or a discharge force is generated at the suction port 323A in the sucking disk head 323. Specifically, when the piston rod 852 is raised, the pressure in the syringe pipe 851 becomes negative to generate the suction force, and when the piston rod 852 is lowered, the discharge force is generated. The sucking disk head 323 is used, for example, to adsorb the black cover 271 when the black cover 271 is moved to the cell sorting portion 23 or the cell transfer portion 26.

Figure 13:
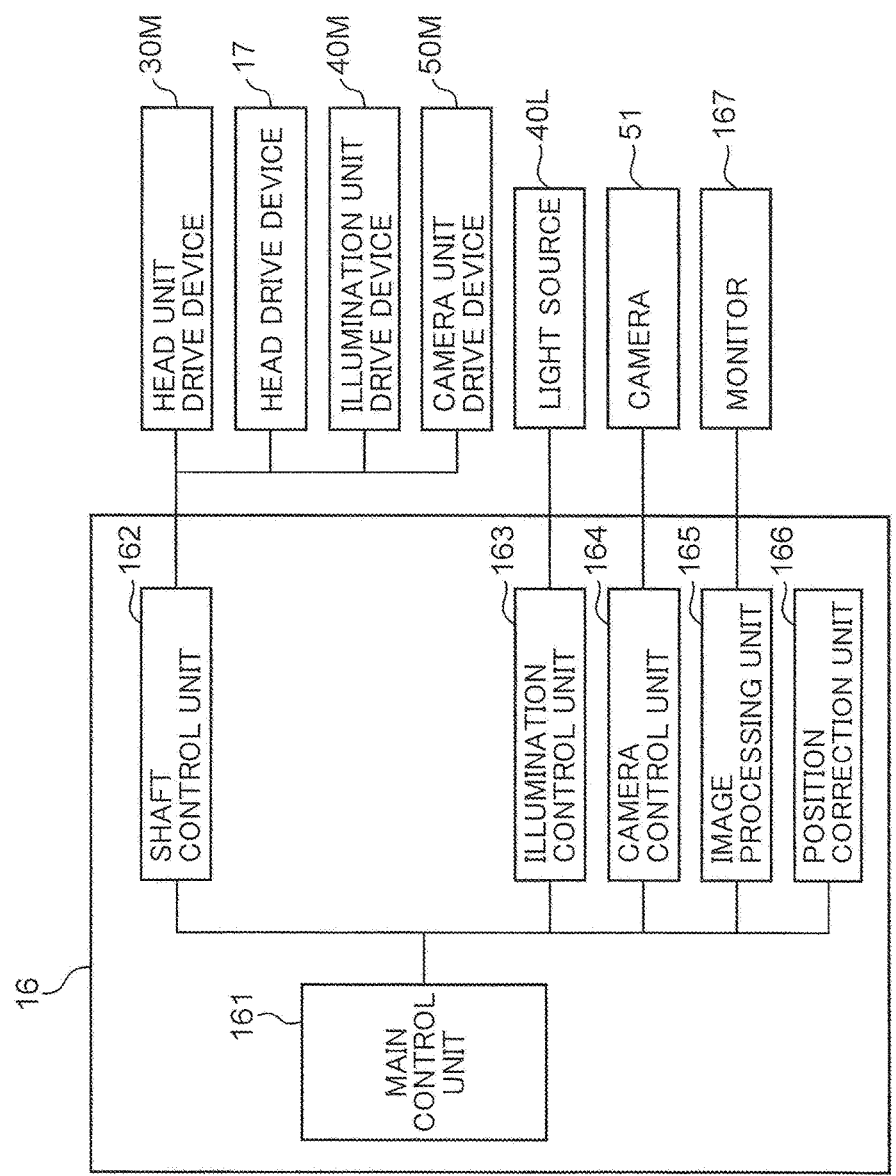
FIG. 13 is a block diagram illustrating a configuration of a control unit of the moving device.

FIG. 13 is a block diagram illustrating the configuration of the control unit 16 of the moving device 1. The control unit 16 functionally includes a main control unit 161, a shaft control unit 162 (control unit), an illumination control unit 163, a camera control unit 164, an image processing unit 165, and a position correction unit 166. The main control unit 161 performs various kinds of control in the apparatus main body 10 of the moving device 1 overall. Specifically, the main control unit 161 moves the head unit 30 (head portion 32) toward each workplace in the cell movement line 20 to perform the operation of mounting and removing the cylinder tip 70 or the dispenser tip 80 and the operation of sucking and discharging the cell culture liquid (cell aggregate), and moves the illumination unit 40 and the camera unit 50 to take an image of a cell aggregate carried on the dish 60 or the microplate 90 or an image of the cylinder tip 70 mounted to the head 33.

The shaft control unit 162 controls the operations of the head unit drive device 30M, the head drive device 17, the illumination unit drive device 40M, and the camera unit drive device 50M. In practice, the shaft control unit 162 controls the first X motor 341 and the first Y motor 361 of the head unit drive device 30M, a drive motor (not shown) included in the head drive device 17, for vertically moving the head 33 (rod 331 and movable cylinder 332), the second X motor 431 and a second Y motor (not shown) of the illumination unit drive device 40M, and the third X motor 541 and the third Y motor 561 of the camera unit drive device 50M.

Specifically, the shaft control unit 162 controls the head unit drive device 30M to control movement of the head unit 30 in the front-back and right-and-left directions. Through the control of the head drive device 17, the vertical movement of the head 33, the first nozzle 321, and the second nozzle 322, the raising and lowering operation of the rod 331 and other members in the head 33 (suction and discharge operation), and the suction and discharge operation in the first nozzle 321 and the second nozzle 322 are controlled. In this embodiment, eight heads 33 (FIG. 8) can be concurrently operated to concurrently execute the operation of mounting the cylinder tip 70 to each head 33, the suction and discharge operation by the cylinder tip 70, and the operation of discarding the cylinder tip 70. Through control of the illumination unit drive device 40M, movement of the illumination unit 40 in the front-back and right-and-left directions is controlled. Through control of the camera unit drive device 50M, movement of the camera unit 50 in the front-back and right-and-left directions is controlled.

The illumination control unit 163 controls a light emitting operation of the light source 40L included in the illumination unit main body portion 42. Specifically, when the camera 51 is used to image a cell aggregate held in the cell sorting portion 23 or the cell transfer portion 26, the illumination control unit 163 turns on and off the light source 40L by a predetermined routine in order to generate transmitted illumination.

The camera control unit 164 controls the imaging operation of the camera 51. For example, the camera control unit 164 controls focusing, shutter timing, and shutter speed (exposure amount) of the camera 51 in the imaging operation.

The image processing unit 165 subjects an image acquired by the camera 51 to image processing, such as shading correction and white balance adjustment. In this embodiment, the image processing unit 165 subjects an image of a cell aggregate acquired in the cell sorting portion 23 or the cell transfer portion 26 to the image processing, and displays the image on the monitor 167. Further, the image processing unit 165 applies a well-known image processing technology to a recognized image of the cylinder tip 70 acquired by the tip imaging portion 25 to determine XY positional information on the suction port 71T in the cylinder tip 70 mounted to the head 33.

The position correction unit 166 performs processing of determining XYZ coordinate positions of the suction port 71T in the cylinder tip 70 mounted to the head 33 on the basis of positional information on the suction port 71T in the XY directions determined by the image processing unit 165 and focus positional information (information acquired by the imaging operation) on the suction port 71T in the Z direction determined by the focusing operation of the camera control unit 164. Then, the position correction unit 166 derives a correction value on the basis of a difference between the XYZ coordinate positions and predetermined reference positions. The shaft control unit 162 refers to the correction value to control the head unit drive device 30M and the head drive device 17, thereby executing the suction and discharge operation of the cylinder tip 70 at the accurate position.

Figure 14:
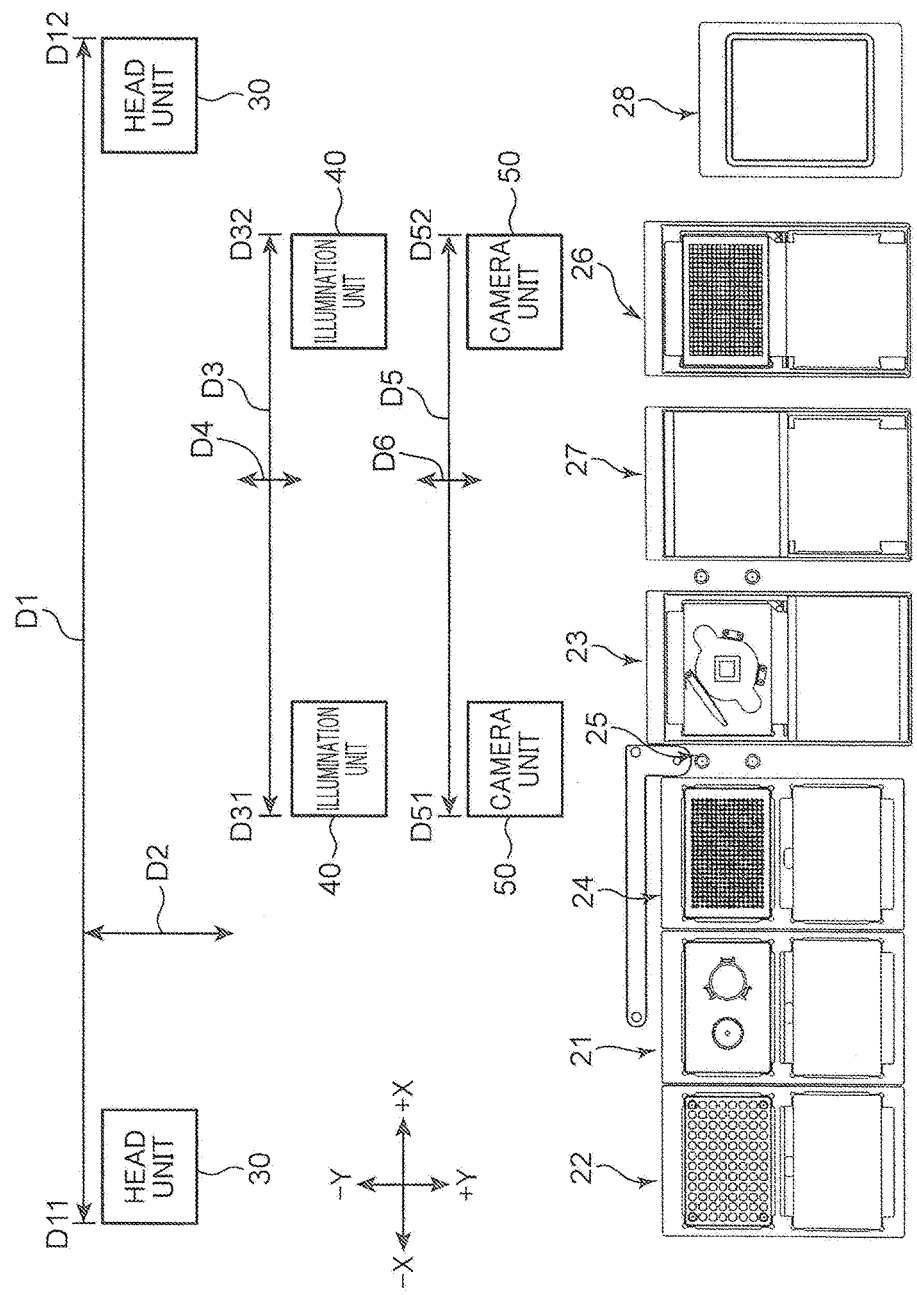
FIG. 14 is a diagram illustrating movement ranges of the head unit, the illumination unit, and the camera unit in the XY direction.

FIG. 14 is a diagram illustrating movement ranges of the head unit 30, the illumination unit 40, and the camera unit 50 in the front-back and left-right directions (XY directions). The workplaces in the cell movement line 20 are arranged side by side in the left-right direction such that the dispenser tip stock portion 22 is arranged on the left end and the tip discarding portion 28 is arranged on the right end. A movement range D1 of the head unit 30 in the left-right direction is set in the range from the left end to the right end of the cell movement line 20 so that the head unit 30 can move above all the workplaces. Specifically, the head unit drive device 30M moves the head unit 30 between a first end portion D11, which is a position at which the work of mounting the dispenser tip 80 can be executed in the dispenser tip stock portion 22, and a second end portion D12, which is a position at which the tip discarding work can be executed in the tip discarding portion 28. Specifically, the first end portion D11 is a position at which the first nozzle 321 of the head portion 32 can be positioned with at least the leftmost dispenser tip 80 retained in the dispenser tip stock portion 22. The second end portion D12 is a position at which the cylinder tip 70 or the dispenser tip 80 mounted to the head portion 32 is opposed to the opening portion 282 in the tip discarding portion 28.

Further, a movement range D2 of the head unit 30 in the front-back direction is set to have such a length that avoids an interference between the head unit 30 and the illumination unit 40. This movement range D2 corresponds to a reciprocating range of the slider arm 38 in the front-back direction. When the head unit 30 and the illumination unit 40 interfere with each other, the head unit drive device 30M controls the slider arm 38 to extend frontward as illustrated in FIG. 3, thereby preventing an interference between the head unit 30 and the illumination unit 40.

A movement range D3 of the illumination unit 40 in the left-right direction is set between the tip imaging portion 25 and the cell transfer portion 26. The illumination unit drive device 40M moves the illumination unit 40 between a third end portion D31, which is located on the left side of a position at which the dish 60 can be irradiated with illumination light in the cell sorting portion 23, and a fourth end portion D32, which is a position at which the well 91 of the microplate 90 can be irradiated with illumination light in the cell transfer portion 26. As apparent from FIG. 14, the movement range D3 is located inside the movement range D1, that is, the third end portion D31 is located on the inner side of the first end portion D11 and the fourth end portion D32 is located on the inner side of the second end portion D12. The dispenser tip stock portion 22, the object stock portion 21, and the tip stock portion 24 exist between the first end portion D11 and the third end portion D31, and the tip discarding portion 28 exists between the second end portion D12 and the fourth end portion D32.

A movement range D5 of the camera unit 50 in the left-right direction is the same as the movement range D3 of the illumination unit 40. Specifically, the movement range D5 of the camera unit 50 is set between the tip imaging portion 25 and the cell transfer portion 26. The camera unit drive device 50M moves the camera unit 50 between a fifth end portion D51, which is a position at which the cylinder tip 70 mounted to the head 33 can be imaged in the tip imaging portion 25, and a sixth end portion D52, which is a position at which a cell aggregate retained in the well 91 of the microplate 90 can be imaged in the cell transfer portion 26.

The illumination unit 40 and the camera unit 50 also have movement ranges D4 and D6 in the front-back direction, respectively. The reason is that the dish 60 and the microplate 90 are members each having the width in the front-back direction as well as in the left-right direction and it is therefore necessary to move the illumination unit 40 and the camera unit 50 in the front-back direction as well in order to illuminate and image all regions of the dish 60 and the microplate 90. Even when a low magnification lens of about 4× is used as the objective lens of the camera unit 50, the field of view area of the lens is about 3 mm×3 mm. On the other hand, the size of the well plate 61 is about 10 mm to 30 mm on one side, and the wells 91 are arranged in a matrix in the microplate 90 at pitches of about 5 mm to 12 mm. Thus, the illumination unit 40 and the camera unit 50 are also required to move in the front-back direction.

The illumination unit drive device 40M moves the illumination unit 40 in the front-back direction by the movement range D4, and the camera unit drive device 50M moves the camera unit 50 in the front-back direction by the movement range D6. The movement ranges D4 and D6 are sufficiently smaller than the movement range D2 of the head unit 30 in the front-back direction. Even when the illumination unit 40 is moved to any position in the movement range D4 in the state in which the slider arm 38 extends most frontward as illustrated in FIG. 3, the illumination unit 40 and the head unit 30 do not interfere with each other.

Figure 15:
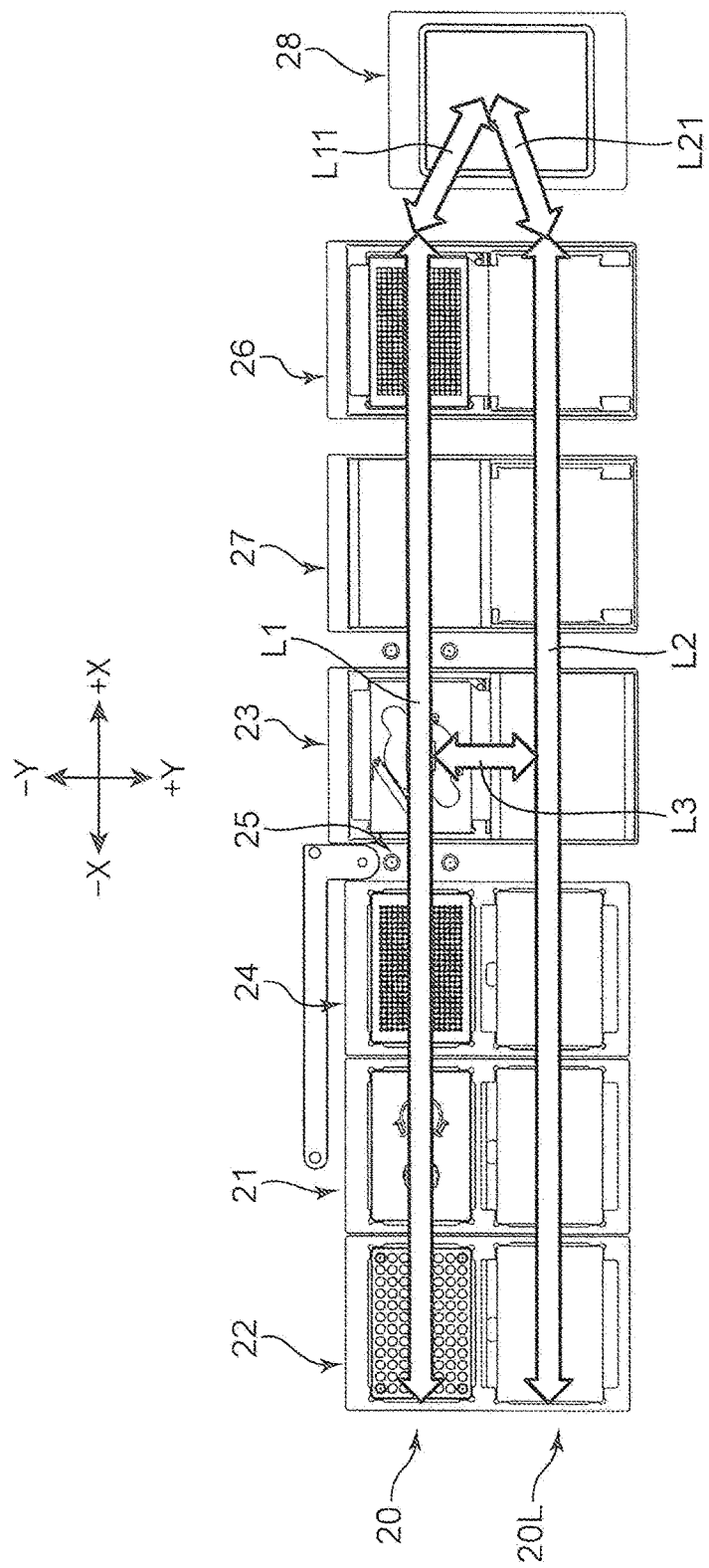
FIG. 15 is a diagram illustrating movement paths of the head unit.

FIG. 15 is a diagram illustrating movement paths that the head unit 30 may take. The head unit 30 can move on a first path L1 that extends linearly in the left-right direction along the cell movement line 20 whose workplaces are arranged side by side in the left-right direction, a linear second path L2 that is in front of the first path L1 and extends in parallel to the first path L1, and a third path L3 that extends in the front-back direction between the first path L1 and the second path L2. In front of each workplace in the cell movement line 20, a placement space 20L in which a lid member configured to cover each workplace is placed, is provided. The first path L1 is a path that is set above the cell movement line 20, and the second path L2 is a path that is set above the placement space 20L.

The third path L3 is a path that is set at an arbitrary position between the first path L1 and the second path L2. FIG. 15 illustrates an example where the third path L3 is set between the cell sorting portion 23 and the lid member placement space 20L in front of the cell sorting portion 23, but the third path L3 may be set above another workplace or between two workplaces.

In this embodiment, only the tip discarding portion 28 is arranged at the position shifted frontward with respect to the other workplaces. Thus, the head unit 30 moves on oblique paths L11 and L21 to move in both the front-back direction and the left-right direction between the right ends of the first path L1 and the second path L2 and the tip discarding portion 28. In FIG. 15, the oblique paths L11 and L21 are simply indicated by oblique arrows, but the actual oblique paths L11 and L21 may be set as a stepped path on which the head unit 30 sequentially moves in the front-back direction and in the left-right direction or an L-shaped path on which the head unit 30 moves to the right end (second end portion D12) on an extended line of the first path L1 or the second path L2 and then moves frontward or backward.

The movement path of the illumination unit 40 in the left-right direction is on the first path L1. The illumination unit 40 moves on the first path L1 in the left-right direction within the movement range D3. The illumination unit 40 can move in the front-back direction in a relatively short range, specifically, move in the front-back direction in a micro range with respect to the first path L1 as its base axis, and the illumination unit 40 cannot move on the second path L2. The movement path of the camera unit 50 in the left-right direction is a path that is set below the base 12 correspondingly to the first path L1. The camera unit 50 moves on this path in the left-right direction within the movement range D5. Similarly, the camera unit 50 can move in the front-back direction in a micro range with the path corresponding to the first path L1 as its base axis.

The shaft control unit 162 controls the head unit drive device 30M to move the head unit 30 on the first path in order to implement works at the plurality of workplaces in the cell movement line 20, which include a work of moving a cell aggregate between the cell sorting portion 23 and the cell transfer portion 26 by using the head 33 and the cylinder tip 70. Further, the shaft control unit 162 controls the illumination unit drive device 40M and the camera unit drive device 50M to move the illumination unit 40 and the camera unit 50 on the first path L1 between the cell sorting portion 23 and the cell transfer portion 26 in order to image a cell aggregate at the cell sorting portion 23 and the cell transfer portion 26. In addition, when the head unit 30 and the illumination unit 40 interfere with each other on the first path L1, the shaft control unit 162 controls the head unit drive device 30M to move the head unit 30 frontward along the third path L3 and move the head unit 30 in the left-right direction on the second path L2.

The head unit drive device 30M is disposed behind (−Y side of) the cell movement line 20. As illustrated in FIG. 3, the slider arm 38 (slider) extends frontward with respect to the first X slider 35. The first path L1 is set on the upstream side of the slider arm 38 in the front advancing direction, and the second path L2 is set on the downstream side thereof. The shaft control unit 162 controls the head unit drive device 30M to move at least the slider arm 38 between a rear position (first position) at which the head unit 30 is positioned with the first path L1 and a front position (second position) at which the head unit 30 is positioned with the second path L2. When the slider arm 38 is located at the front position, the illumination unit 40 can move on the first path L1 without interfering with the head unit 30.

As described above with reference to FIG. 14, the movement range D3 of the illumination unit 40 in the left-right direction is inside the movement range D1 of the head unit 30 in the left-right direction. Specifically, the third end portion D31 and the fourth end portion D32 are set at positions at which the illumination unit 40 does not interfere with the head unit 30 even when the illumination unit 40 moves on the first path L1 in the state where the head unit 30 is located at least the first end portion D11 or the second end portion D12 on the first path L1. In this embodiment, in the state in which the head unit 30 is located on the first path L1 (including the oblique path L11) at the dispenser tip stock portion 22, the object stock portion 21, the tip stock portion 24, or the tip discarding portion 28, the head unit 30 and the illumination unit 40 do not interfere with each other even when the illumination unit 40 is located at any position on the first path L1.

On the other hand, when the head unit 30 is located on the first path L1 at the workplaces other than the above, the head unit 30 and the illumination unit 40 interfere with each other. In this case, the shaft control unit 162 controls the head unit drive device 30M to retreat the head unit 30 onto the second path L2. Then, the shaft control unit 162 controls the head unit drive device 30M and the illumination unit drive device 40M to move the illumination unit 40 in the left-right direction along the first path L1 and move the head unit 30 in the left-right direction along the second path L2 so that the illumination unit 40 and the head unit 30 pass each other, thereby moving the illumination unit 40 and the head unit 30 to desired workplaces efficiently. A specific example of this control is now described.

Operations (works) to be executed by the apparatus main body 10 of the moving device 1 under control of the control unit 16 are roughly divided into an operation of dispensing a cell culture liquid with use of the dispenser tip 80 and a cell movement operation with use of the cylinder tip 70. The dispensing operation includes the following Work Steps 1 to 5 that are executed in sequence.

(Work Step 1) Move the head unit 30 to above the dispenser tip stock portion 22, and mount the dispenser tip 80 to the first nozzle 321 of the head portion 32.

(Work Step 2) Move the head unit 30 to above the object stock portion 21, and suck a predetermined dispensed amount of a cell culture liquid containing a cell aggregate, which is stored in the tube 212, into the dispenser tip 80.

(Work Step 3) Move the head unit 30 to above the cell sorting portion 23, and discharge the cell culture liquid in the dispenser tip 80 to the dish 60.

(Work Step 4) Move the illumination unit 40 and the camera unit 50 to above and below the cell sorting portion 23, respectively, and image the dish 60 where the cell culture liquid is dispensed.

(Work Step 5) Move the head unit 30 to above the tip discarding portion 28, remove the used dispenser tip 80 from the first nozzle 321, and discard the dispenser tip 80 in the collection box 281.

The cell movement operation includes the following Work Steps 6 to 11.

(Work Step 6) Move the head unit 30 to above the tip stock portion 24, and mount the cylinder tip 70 to the head 33.

(Work Step 7) Move the head unit 30 and the camera unit 50 to above and below the tip imaging portion 25, respectively, image the cylinder tip 70 mounted to the head 33, and determine XYZ coordinate positions of the suction port 71T in the cylinder tip 70 on the basis of the acquired image.
(Work Step 8) Move the head unit 30 to above the cell sorting portion 23, and suck the cell aggregate stored in the dish 60 into the cylinder tip 70.
(Work Step 9) Move the head unit 30 to above the cell transfer portion 26, and discharge the cell aggregate in each cylinder tip 70 to the well 91 of the microplate 90.
(Work Step 10) Move the head unit 30 to above the tip discarding portion 28, remove the used cylinder tip 70 from the head 33, and discard the cylinder tip 70 in the collection box 281.
(Work Step 11) Move the illumination unit 40 and the camera unit 50 to above and below the cell transfer portion 26, and image the cell aggregate in the well 91.

Figure 16:
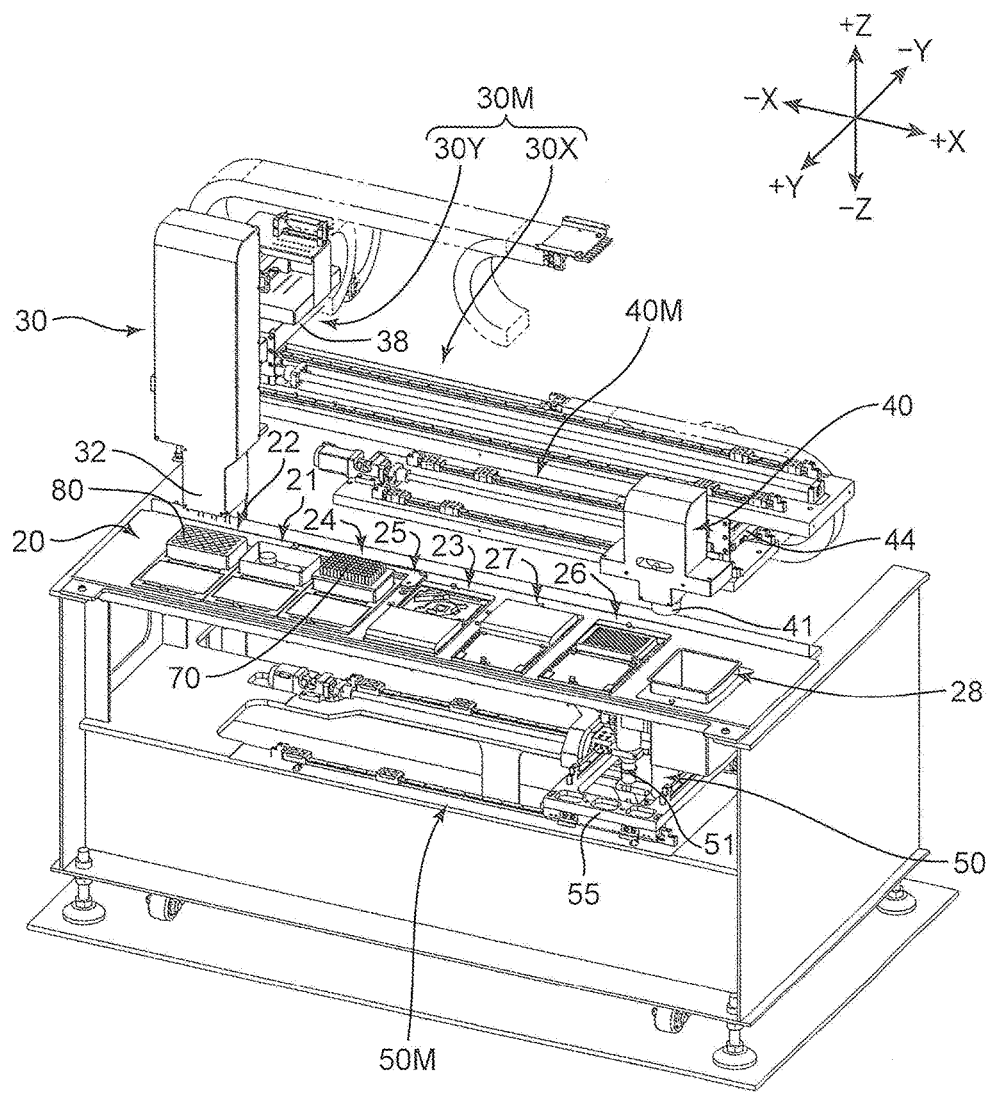
FIG. 16 is a perspective view illustrating one step in an object movement work executed by the head unit, the illumination unit, and the camera unit.

Referring to FIG. 16 to FIG. 27 and FIG. 14 and FIG. 15 referred to above, the positional relation among the head unit 30, the illumination unit 40, and the camera unit 50 during the execution of Work Steps 1 to 10 is now described. FIG. 16 is a view illustrating the state in which "Work Step 1" is executed. FIG. 17 is a side view of the head unit 30, the illumination unit 40, and the camera unit 50 in the state in which "Work Step 1" is executed as viewed from the right direction.

At "Work Step 1", the shaft control unit 162 controls the head unit drive device 30M to move the head unit 30 on the first path L1 to the vicinity of the first end portion D11 (-X limit) of the movement range D1. The shaft control unit 162 further controls the illumination unit drive device 40M to move the illumination unit 40 on the first path L1 to the fourth end portion D32 (+X limit) of the movement range D3. The shaft control unit 162 further controls the camera unit drive device 50M to move the camera unit 50 to the sixth end portion D52 (+X limit) of the movement range D5 so as to follow the illumination unit 40. In "Work Step 1", both of the head unit 30 and the illumination unit 40 are located on the first path L1, and hence have a positional relation in which the head unit 30 and the illumination unit 40 completely overlap with each other in side view as illustrated in FIG. 17. However, the head unit 30 and the illumination unit 40 are arranged at positions away from each other in the left-right direction and do not therefore interfere with each other.

At "Work Step 1", the shaft control unit 162 controls the head unit drive device 30M to position the head unit 30 above the dispenser tip stock portion 22, and then controls the head drive device 17 to lower the first nozzle 321 of the head portion 32 and mount the dispenser tip 80 to the lower end of the first nozzle 321. The specific operation is as described above with reference to FIG. 11A and FIG. 11B. At this time, the illumination unit 40 and the camera unit 50 are in the suspended state.

For executing "Work Step 2", the shaft control unit 162 moves the head unit 30 rightward from the state in FIG. 16 and stops the head unit 30 above the object stock portion 21. This stop position is a position at which the first nozzle 321 is located directly above the upper opening in the tube 212. Next, the shaft control unit 162 controls the head drive device 17 to lower the first nozzle 321 so that the lower end portion 82 (FIG. 11C) of the dispenser tip 80 is immersed in a cell culture liquid containing a cell aggregate stored in the tube 212. Then, the shaft control unit 162 further controls the head drive device 17 to generate a suction force from the first nozzle 321 so that the dispenser tip 80 sucks a predetermined dispensing amount of the cell culture liquid stored in the tube 212. After that, the first nozzle 321 is raised.

For executing "Work Step 3", the shaft control unit 162 moves the head unit 30 more rightward so that the first nozzle 321 is located above the dish 60 in the cell sorting portion 23. The head unit 30 may be moved rightward simply on the first path L1, but may take a route bypassing the space above the tip stock portion 24. In this case, the head unit 30 is controlled to take a route such that the head unit 30 is moved from the first path L1 toward the second path L2, moved rightward on the second path L2 to the position corresponding to the cell sorting portion 23, and moved backward on the third path L3. This configuration can avoid liquid drip from the dispenser tip 80 sucking the cell culture liquid to the tip stock portion 24. After that, the shaft control unit 162 controls the head drive device 17 to lower the first nozzle 321 toward the dish 60 and further controls the first nozzle 321 to generate a discharge force, thereby discharging the cell culture liquid in the dispenser tip 80 to the dish 60. After that, the first nozzle 321 is raised. Also during the execution of "Work Step 2" and "Work Step 3", the illumination unit 40 and the camera unit 50 are in the suspended state at the same positions as in FIG. 16.

Figure 18:
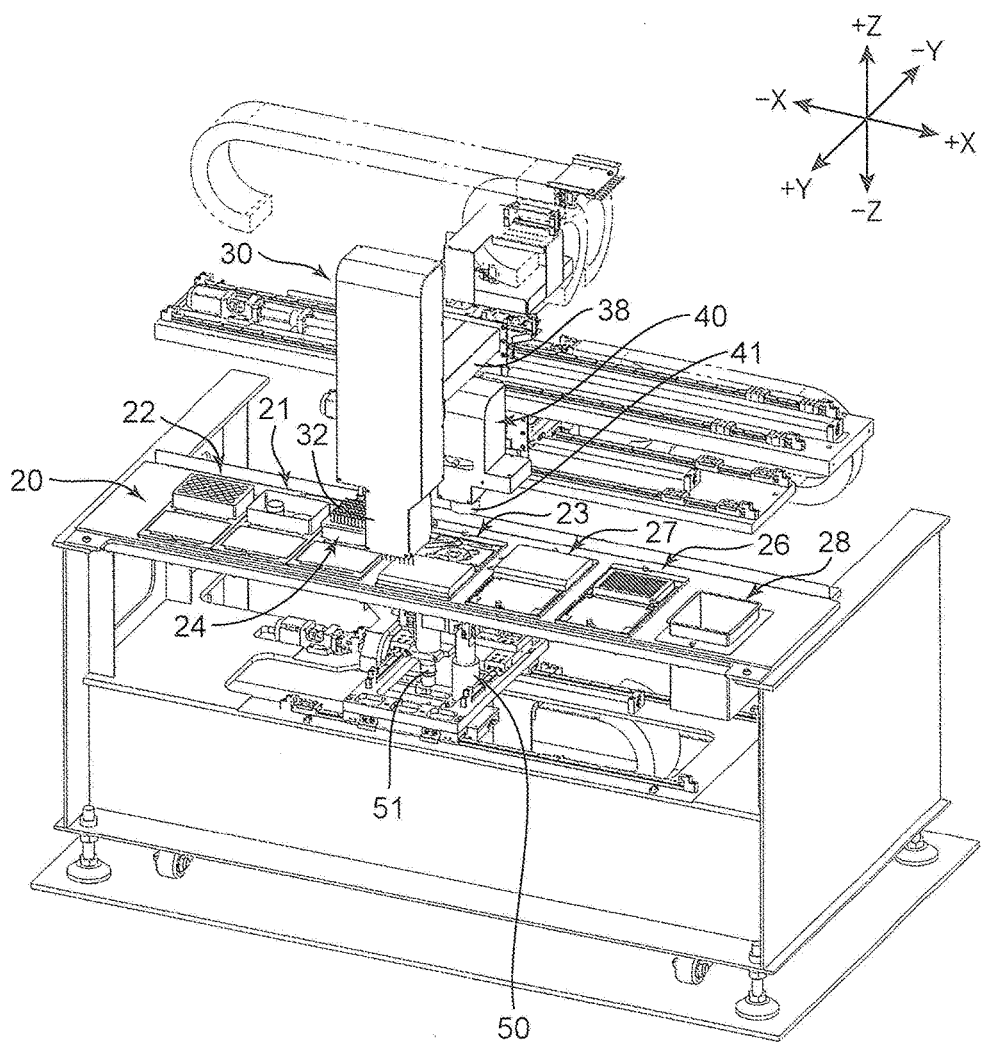
FIG. 18 is a perspective view illustrating one step in the movement work.

For executing "Work Step 4", as illustrated in FIG. 18, the shaft control unit 162 moves the head unit 30 in the front direction from the cell sorting portion 23 to retreat the head unit 30 onto the second path L2. Further, the shaft control unit 162 controls the illumination unit drive device 40M and the camera unit drive device 50M to move the illumination unit 40 and the camera unit 50 to the arrangement positions for the cell sorting portion 23 on the first path L1. The positional relation of the units 30, 40, and 50 in side view in the state in FIG. 18 is as illustrated in FIG. 3. Such a retreating operation of the head unit 30 can avoid an interference between the head unit 30 and the camera unit 50 even when the head unit 30 and the camera unit 50 are located at the same position in the left-right direction.

At "Work Step 4", an image of the dish 60 (well plate 61) is acquired in order to check how a cell aggregate is carried on the well plate 61 (FIG. 6). The image is taken in a manner that the illumination unit 40 emits transmitted illumination and the camera 51 images the well plate 61 under control of the illumination control unit 163 and the camera control unit 164. For this imaging, the shaft control unit 162 moves the illumination unit 40 and the camera unit 50 in the front-back direction within the movement ranges D4 and D6 as necessary.

Then, the image processing unit 165 executes image processing on the taken image, and it is confirmed based on the resultant image whether or not a cell aggregate is satisfactorily carried in each recess 61C. This is a process for confirming in which position on the well plate 61 the cell aggregate satisfying predetermined conditions (size, shape, etc.) is present (which of the recesses 61C the cell aggregate is carried on). When a satisfactory carrying state is confirmed, the work of discarding the dispenser tip 80 in "Work Step 5 is executed. The arrangement of the units 30, 40, and 50 during the execution of "Work Step 5" is described later. Note that, if the carried state is poor, measures are taken to dispense the cell culture liquid again or vibrate the dish 60.

Next, for executing "Work Step 6" in the cell movement operation, the shaft control unit 162 moves the head unit 30 to above the tip stock portion 24. At this time, the shaft control unit 162 moves the illumination unit 40 and the camera unit 50 to the fourth end portion D32 and the sixth end portion D52 (+X limit) similarly to the example illustrated in FIG. 16. After that, the shaft control unit 162 controls the head drive device 17 to lower the head 33 of the head portion 32 and mount the cylinder tip 70 to the lower end of the head. The specific operation is as described above with reference to FIG. 9.

Figure 19:
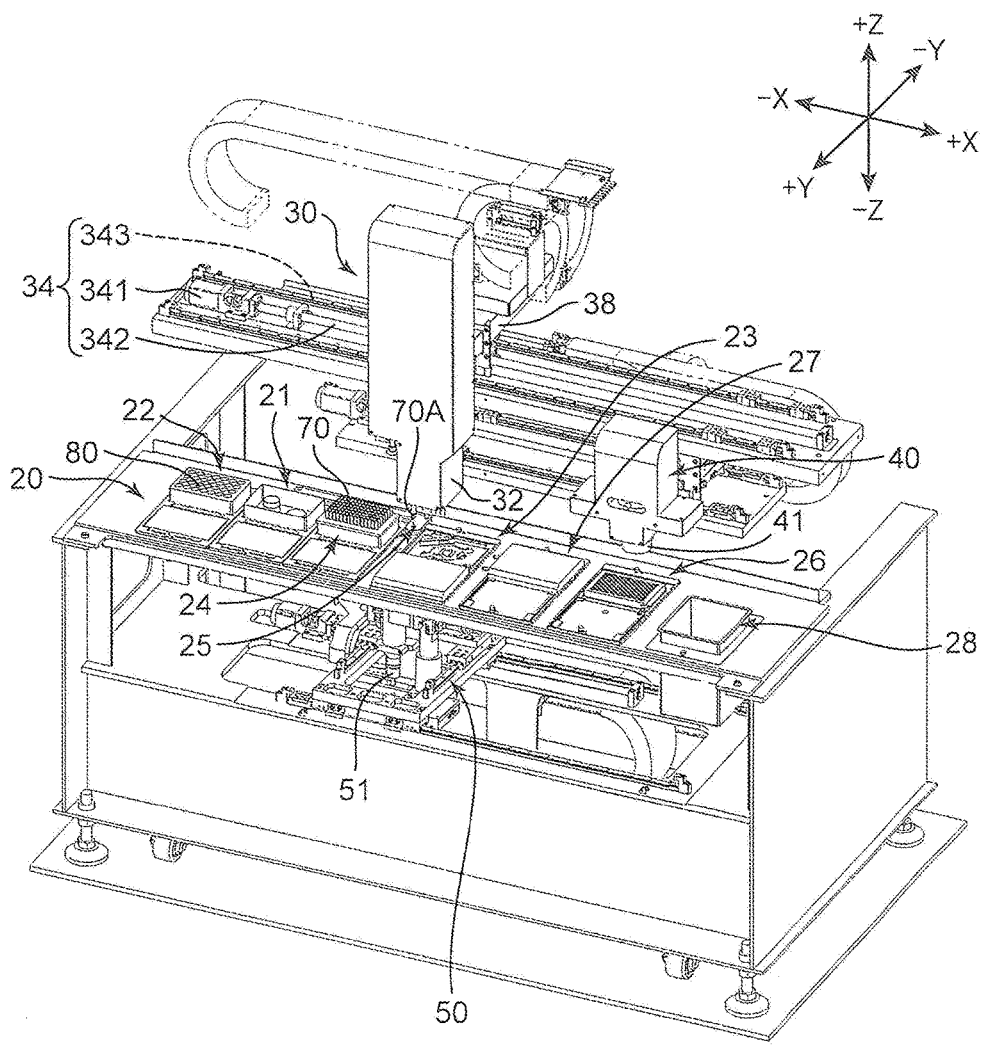
FIG. 19 is a perspective view illustrating one step in the movement work.

For executing "Work Step 7", the shaft control unit 162 controls the head unit drive device 30M to move the head unit 30 above the tip imaging portion 25 as illustrated in FIG. 19. The shaft control unit 162 further controls the camera unit drive device 50M to move the camera unit 50 directly below the tip imaging portion 25, that is, to the vicinity of the fifth end portion D51 (−X limit). The illumination unit 40 is moved above the cell transfer portion 26 to be positioned with the cell transfer portion 26. After that, the shaft control unit 162 lowers one head 33 to which the cylinder tip 70A to be imaged is mounted. Further, the camera control unit 164 controls the camera 51 to take an image of the cylinder tip 70A. At this time, the illumination control unit 163 turns on the epi-illumination device (or turns on an LED illumination device incorporated in the tip imaging portion 25) for illuminating the cylinder tip 70A.

Specifically, the cylinder tip 70 is lowered to the imaging range, and thereafter the head 33 is lowered at constant pitches, for example, in increments of 10 μm, and the cylinder tip 70A is imaged by the camera 51 every time. In this case, the plunger main body portion 722 is deeply inserted in the syringe main body portion 712 so that the distal end portion 724 (FIG. 9) of the plunger 72 and the suction port 71T are aligned with each other. The reason is that this state is generally the state of starting to suck a cell aggregate, and the position of the suction port 71T shifts depending on the insertion state of the plunger main body portion 722. Note that, in order not to damage a cell aggregate, the distal end portion 724 of the plunger 72 may be raised to be slightly higher than the suction port 71T in some cases after the cylinder tip 70 is immersed in the cell culture liquid and before the cell aggregate is started to be sucked. An image with the highest contrast is selected as a focused image from among a plurality of images acquired by the imaging, and the Z coordinate position of the suction port 71T is determined on the basis of focus positional information at the time when the focused image is acquired. Further, the focused image is subjected to image processing to determine the XY coordinate positions of the suction port 71T. On the basis of a difference between the XYZ coordinate positions and predetermined reference positions, a correction value representing a shift with respect to the distal end of the rod 331 is derived. The same imaging operation and correction value deriving operation as described above are performed for cylinder tips 70 mounted to the other heads 33.

Figure 20:
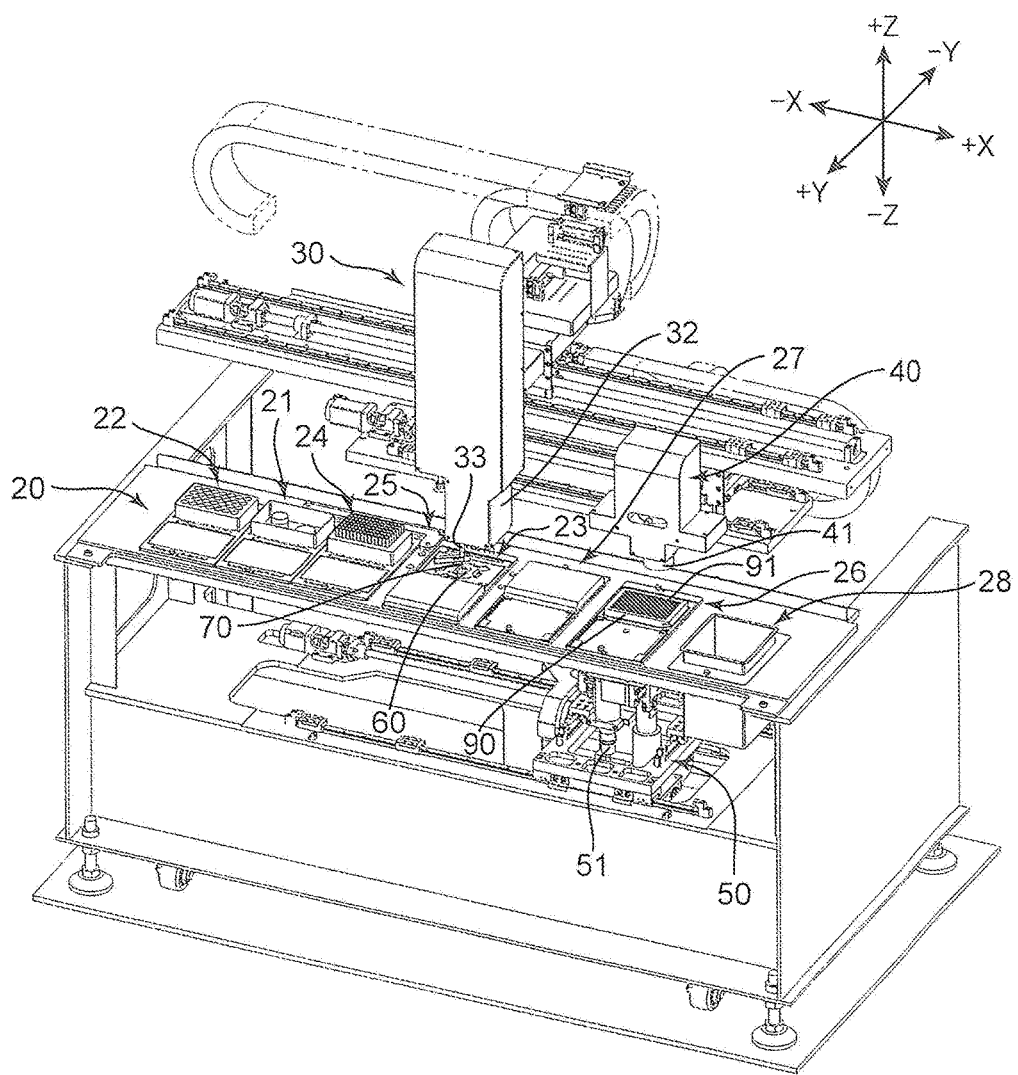
FIG. 20 is a perspective view illustrating one step in the movement work.

FIG. 20 illustrates the state in which "Work Step 8" is executed. In "Work Step 8", the shaft control unit 162 moves the head unit 30 from the tip imaging portion 25 above the cell sorting portion 23 and stops the head unit 30 at the position at which one head 33 is opposed to a predetermined position of the dish 60. The predetermined position is a position above one recess 61C of the well plate 61, which is obtained by imaging of the dish 60 at "Work Step 4" and subsequent image processing and which houses a cell aggregate to be sucked.

After that, the shaft control unit 162 controls the head drive device 17 to lower the one head 33 toward the dish 60. Then, a cell aggregate to be sucked is sucked into the cylinder tip 70 together with the cell culture liquid by the method described with reference to FIGS. 10A to 10D. After that, the one head 33 is raised. Subsequently, the same operation is sequentially performed on the remaining heads.

Note that when a cell aggregate that is expected to have poor suction efficiency is a suction target, the dish 60 is imaged after the suction operation. When unsucked cell aggregates are left in the dish 60, the suction is retried by the cylinder tip 70.

For these operations, the shaft control unit 162 controls the camera unit drive device 50M to move the camera unit 50 rightward so that the camera unit 50 is positioned directly below the cell transfer portion 26. Note that the illumination unit 40 has already been positioned above the cell transfer portion 26. This operation is performed when a cell aggregate has already been carried in the microplate 90, and performed for controlling the camera 51 to image the microplate 90 in order to grasp how the cell aggregate is carried in the microplate 90. Under control of the illumination control unit 163 and the camera control unit 164, the illumination unit 40 emits transmitted illumination and the camera 51 images the microplate 90. On the basis of the image acquired in this imaging, an empty well 91 is confirmed, and the movement destination of the next cell aggregate is recognized. Alternatively, on the basis of the image, it is simply confirmed whether the cell aggregate has been satisfactorily discharged to the microplate 90 or not.

As illustrated in FIG. 18 to FIG. 20, according to this embodiment, the work of positioning the head unit 30 with the cell sorting portion 23 (first container) via the second path L2 in order to suck a cell aggregate with the cylinder tip 70 and the work of positioning the illumination unit 40 and the camera unit 50 with the microplate 90 (second container) in order to image the microplate 90 at the cell transfer portion 26 can be executed concurrently. Consequently, work efficiency can be improved.

Figure 21:
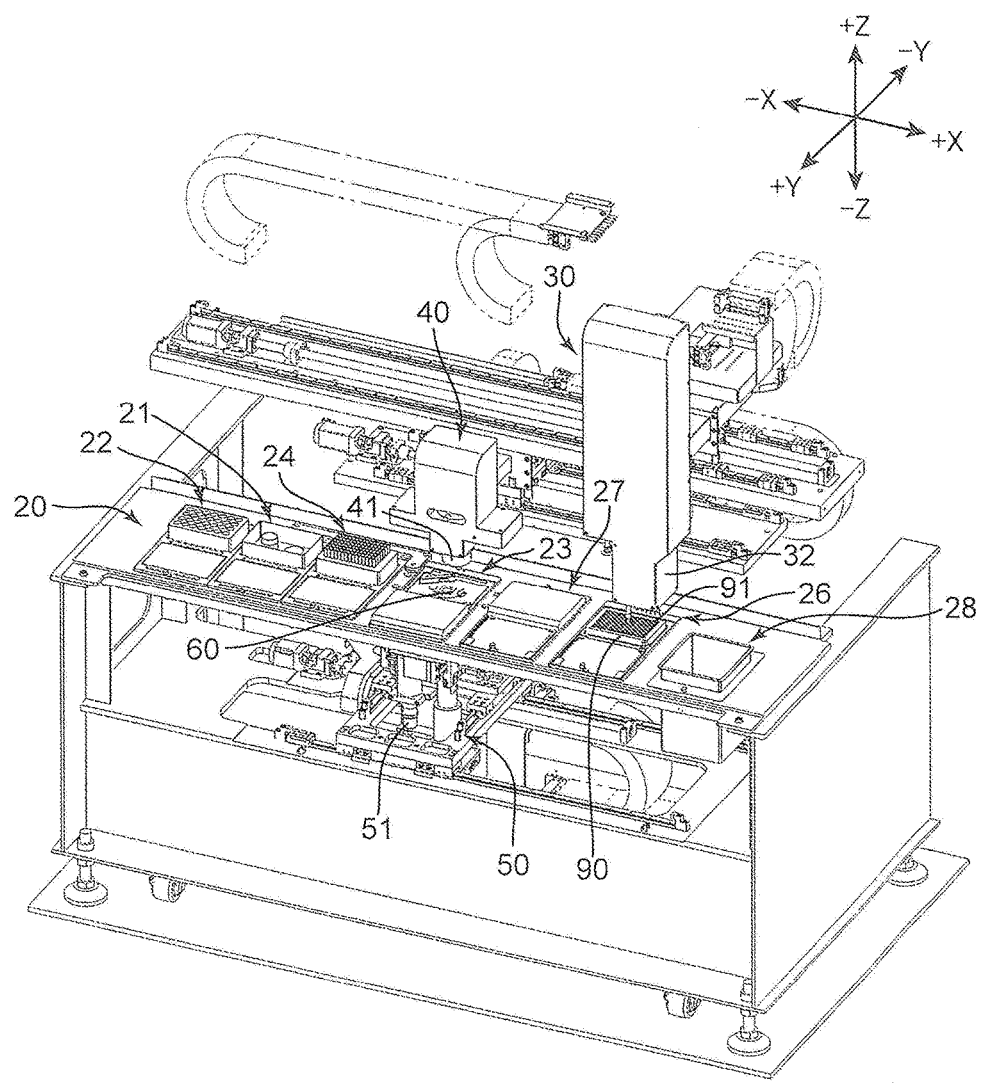
FIG. 21 is a perspective view illustrating one step in the movement work.

FIG. 21 illustrates the state in which "Work Step 9" is executed. After "Work Step 8", the shaft control unit 162 moves the head unit 30 from the cell sorting portion 23 onto the cell transfer portion 26, and moves the illumination unit 40 from the cell transfer portion 26 onto the cell sorting portion 23. In this case, the shaft control unit 162 once moves the head unit 30 in the front direction on the third path L3 from the first path L1 toward the second path L2, moves the head unit 30 in the right direction on the second path L2, and thereafter moves the head unit 30 in the back direction to be stopped above the cell transfer portion 26. In this manner, the shaft control unit 162 moves the illumination unit 40 leftward on the first path L1 and stops the illumination unit 40 above the cell sorting portion 23 while bypassing the head unit 30 to the second path L2. In this manner, the head unit 30 and the illumination unit 40 both of which are arranged above the base 12 are moved so that the head unit 30 and the illumination unit 40 pass each other, and hence the head unit 30 and the illumination unit 40 do not interfere with each other, and one of the head unit 30 and the illumination unit 40 does not need to wait for the other. Note that the shaft control unit 162 also moves the camera unit 50 directly below the cell sorting portion 23 at the timing of moving the illumination unit 40.

After that, the shaft control unit 162 controls the head drive device 17 to concurrently lower eight heads 33 of the head portion 32 toward the microplate 90. Then, cell aggregates in the cylinder tips 70 are concurrently discharged to the respective wells 91 by the method described with reference to FIG. 10E. It should be understood that cell aggregates may be sequentially discharged from the cylinder tips 70 one by one rather than being concurrently discharged. On the other hand, under control of the illumination control unit 163 and the camera control unit 164, the illumination unit 40 emits transmitted illumination and the camera 51 images the well plate 61. In this manner, positional information on a cell aggregate housed (remaining) in the cell sorting portion 23 can be acquired.

Figure 22:
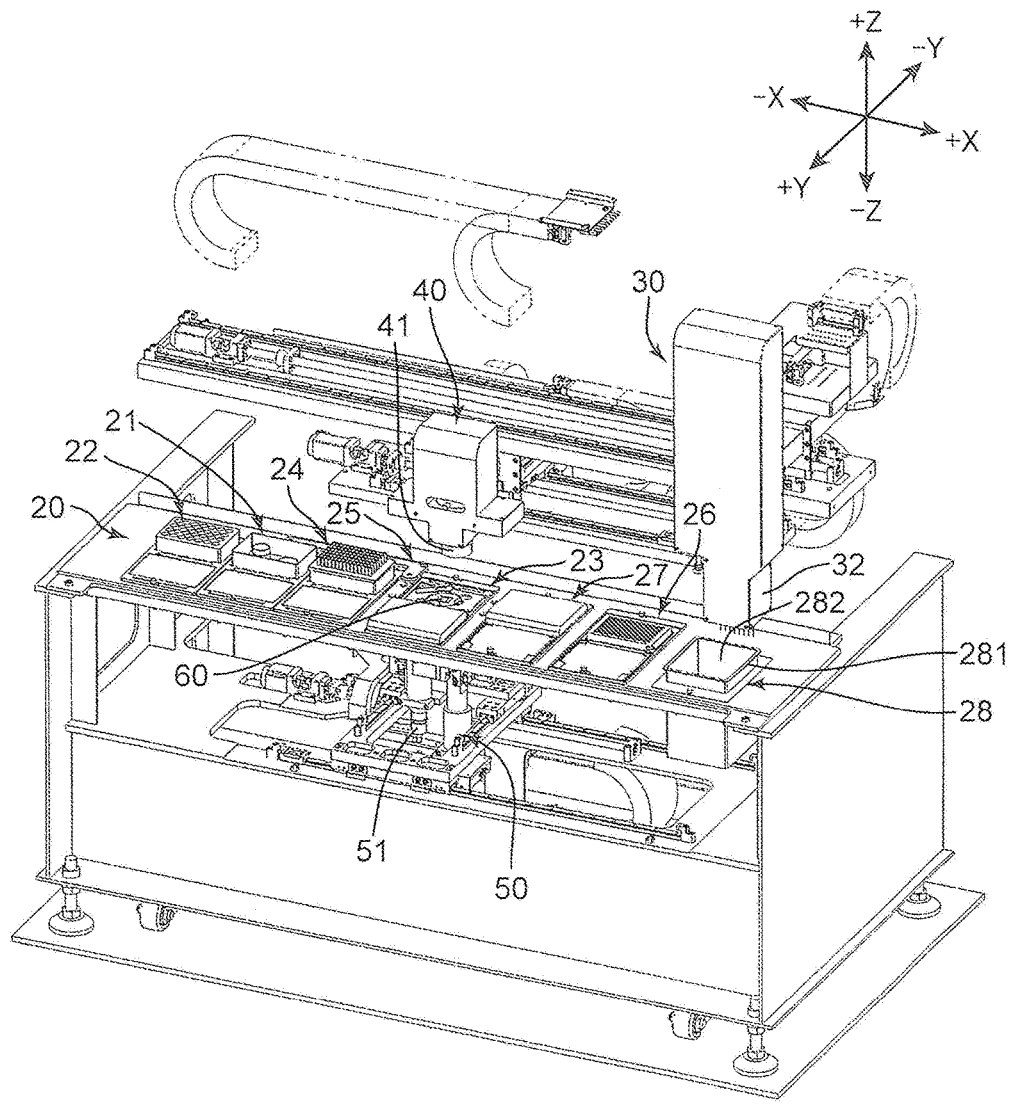
FIG. 22 is a perspective view illustrating one step in the movement work.

FIG. 22 illustrates the state in which "Work Step 10" is executed. After "Work Step 9", the shaft control unit 162 moves the head unit 30 from the cell transfer portion 26 above the tip discarding portion 28. During this movement, the head unit 30 moves on the oblique path L11 described with reference to FIG. 15. After the shaft control unit 162 stops the head unit 30 above the tip discarding portion 28, the shaft control unit 162 controls the head drive device 17 to remove the cylinder tip 70 from the head 33 by the method described above with reference to FIG. 9, and discard the cylinder tip 70 in the collection box 281. Note that, in the case where a cell aggregate is discharged from the cylinder tip 70 to the microplate 90, the cylinder tip 70 is not always required to be discarded for each discharge unless chemicals or the like adhere to the cylinder tip 70.

For executing "Work Step 5" of discarding the dispenser tip, the shaft control unit 162 moves the head unit 30 from the cell sorting portion 23 to the second path L2 via the third path L3, move the head unit 30 in the right direction on the second path L2, and then move the head unit 30 to above the tip discarding portion 28 via the oblique path L21. After that, the shaft control unit 162 controls the head drive device 17 to remove the dispenser tip 80 from the first nozzle 321 by the method described above with reference to FIGS. 10C and 10D, and discard the dispenser tip 80 in the collection box 281.

Figure 23:
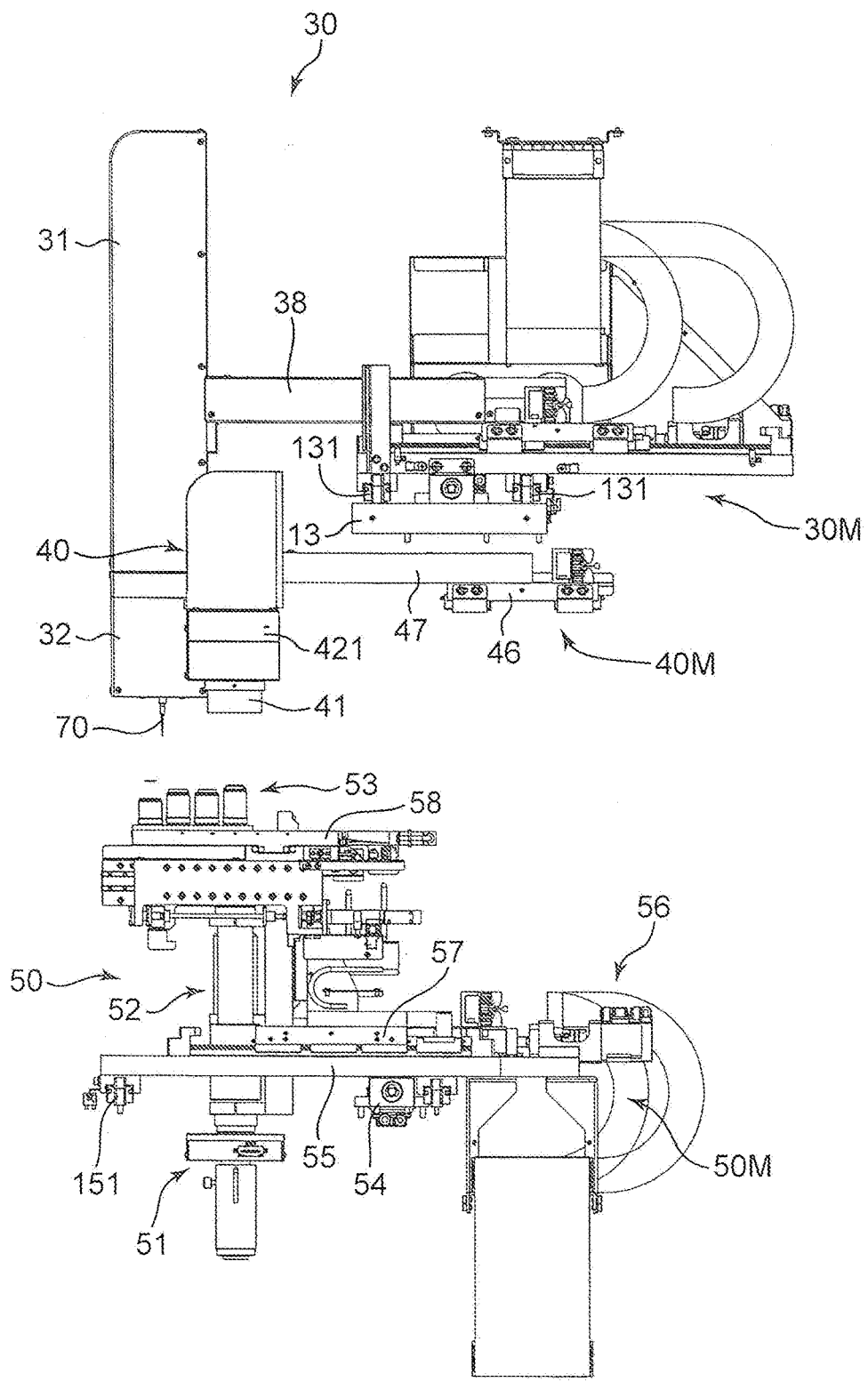
FIG. 23 is a side view of the head unit, the illumination unit, and the camera unit as viewed from the +X direction in a state in which the work step in FIG. 22 is executed.

FIG. 23 is a side view illustrating an arrangement relation between the head unit 30 and the illumination unit 40 in the state in which "Work Step 10" or "Work Step 5" is executed. In FIG. 23, the illumination unit 40 is placed on the front side for easier understanding. In this state, the head unit 30 retreats frontward insufficiently, and the head unit 30 and the illumination unit 40 have a positional relation in which the head unit 30 and the illumination unit 40 interfere with each other.

Figure 24:
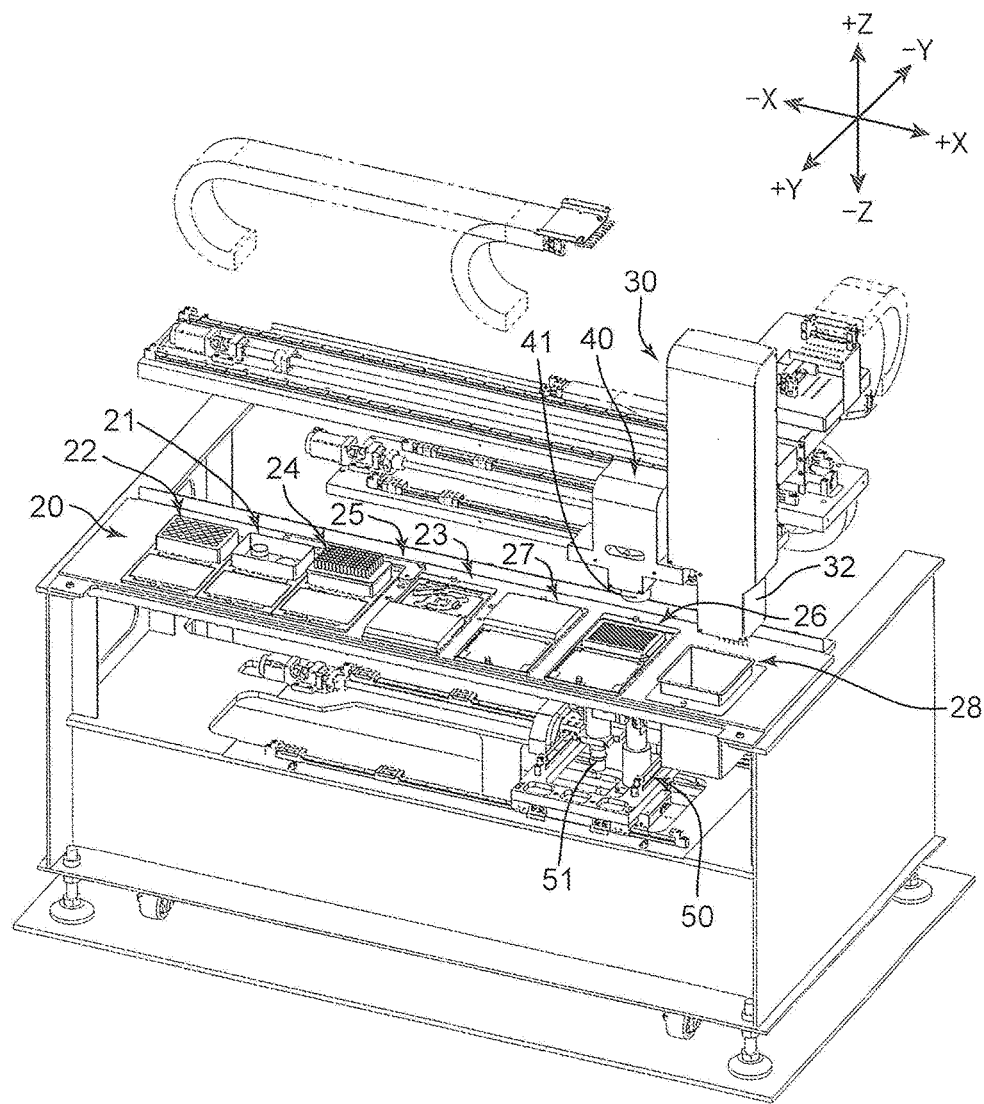
FIG. 24 is a perspective view illustrating one step in the movement work.

FIG. 24 illustrates the state in which "Work Step 11" is executed. After "Work Step 10", the shaft control unit 162 moves the illumination unit 40 and the camera unit 50 from the cell sorting portion 23 to the cell transfer portion 26. The shaft control unit 162 may move the illumination unit 40 and the camera unit 50 during the execution of "Work Step 10". This movement makes the head unit 30 and the illumination unit 40 closest to each other.

Figure 25:
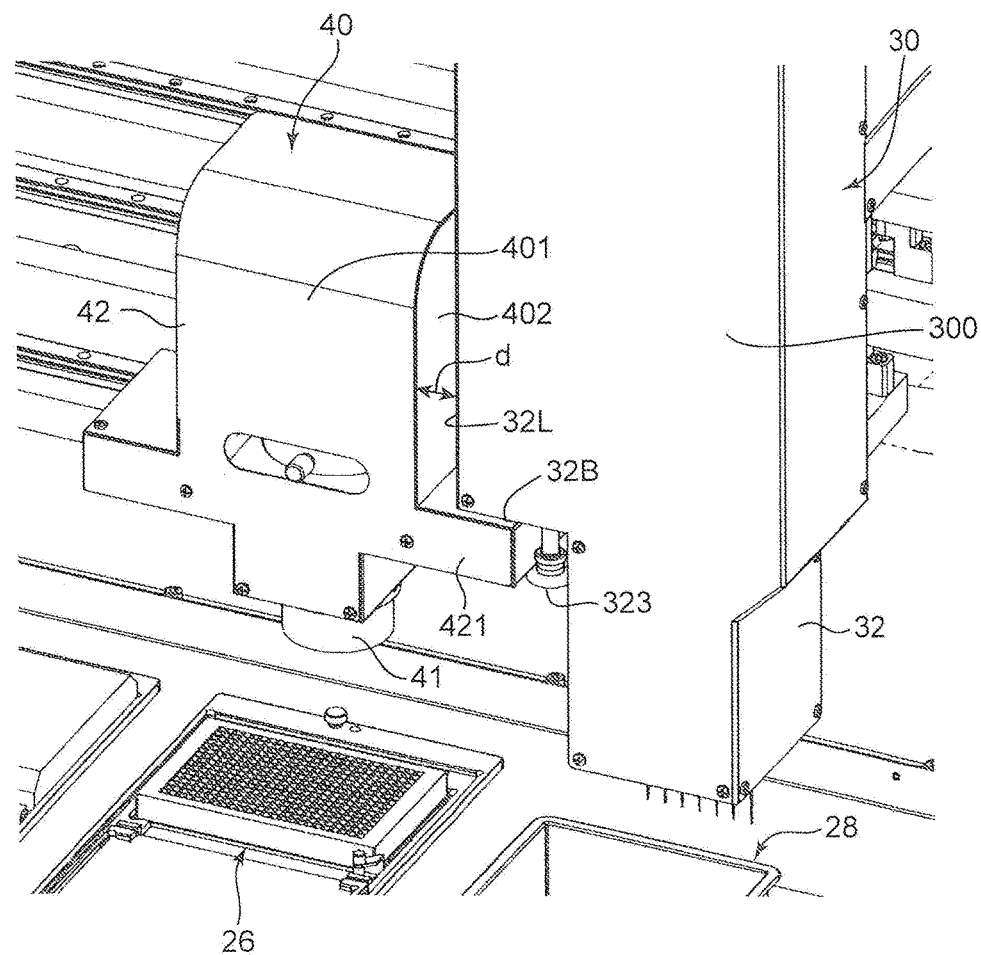
FIG. 25 is an enlarged perspective view of the head unit and the illumination unit in a state in which the work step in FIG. 24 is executed.

FIG. 25 is an enlarged perspective view of the head unit 30 and the illumination unit 40 in the state of FIG. 24. As described above, the illumination unit main body portion 42 of the illumination unit 40 has a protruding portion 421 serving as a retreat destination of the optical filter. A housing 300 of the head unit 30 has a left wall 32L formed of a vertical flat wall. A lower end of the left wall 32L does not reach a lower end surface of the head portion 32, and extends only to an intermediate lower end surface 32B that is above the lower end surface of the head portion 32. Therefore, a housing space exists in the vicinity of the lower left end of the head unit 30.

A housing 401 of the illumination unit main body portion 42 has a right wall 402 formed of a vertical flat wall. A protruding portion 421 on the right side protrudes rightward from a lower end of the right wall 402. The protruding portion 421 enters the housing space in a manner that a top surface of the protruding portion 421 on the right side comes close to the intermediate lower end surface 32B. Note that the protruding portion 421 enters the housing space to a position at which a right side surface of the protruding portion 421 does not interfere with the sucking disk head 323. This arrangement can reduce the distance d between the left wall 32L and the right wall 402, thereby bringing the head unit 30 and the illumination unit 40 having the protruding portion 421 into close contact with each other while preventing the interference between the head unit 30 and the illumination unit 40. Consequently, the moving device 1 can be downsized, and the illumination unit 40 and the head unit 30 can perform their corresponding works at the cell transfer portion 26 and the tip discarding portion 28 adjacent to each other.

At "Work Step 11", the microplate 90 is imaged in order to check whether or not a cell aggregate has been successfully discharged. The camera 51 takes an image of the microplate 90 under control of the illumination control unit 163 and the camera control unit 164. The taken image is subjected to image processing by the image processing unit 165 and displayed on the monitor 167. When a cell aggregate is carried on the well 91 of the microplate 90 designated as a discharge target, the discharge is determined to be successful. When no cell aggregate is carried on the well 91, the well 91 is designated as a discharge target again.

Figure 26:
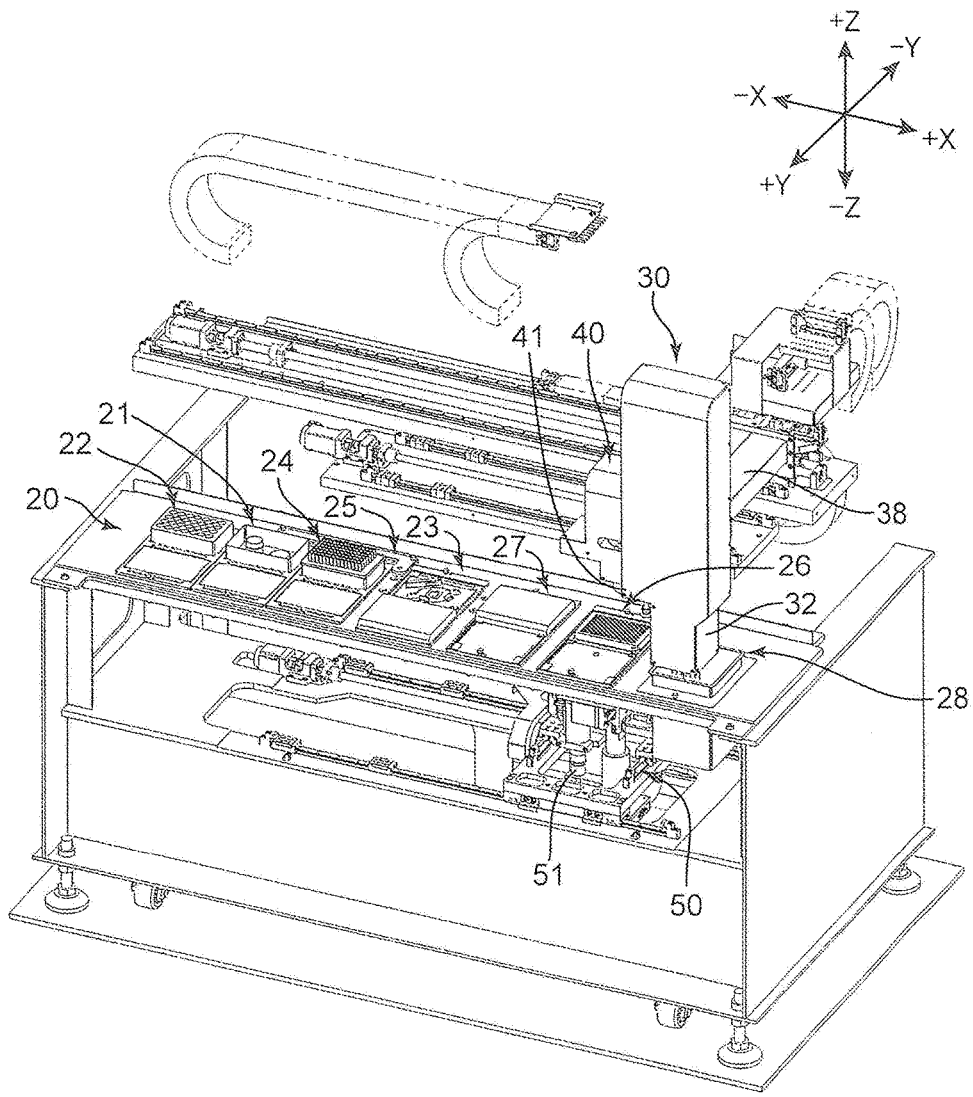
FIG. 26 is a perspective view illustrating one step in the movement work.
Figure 27:
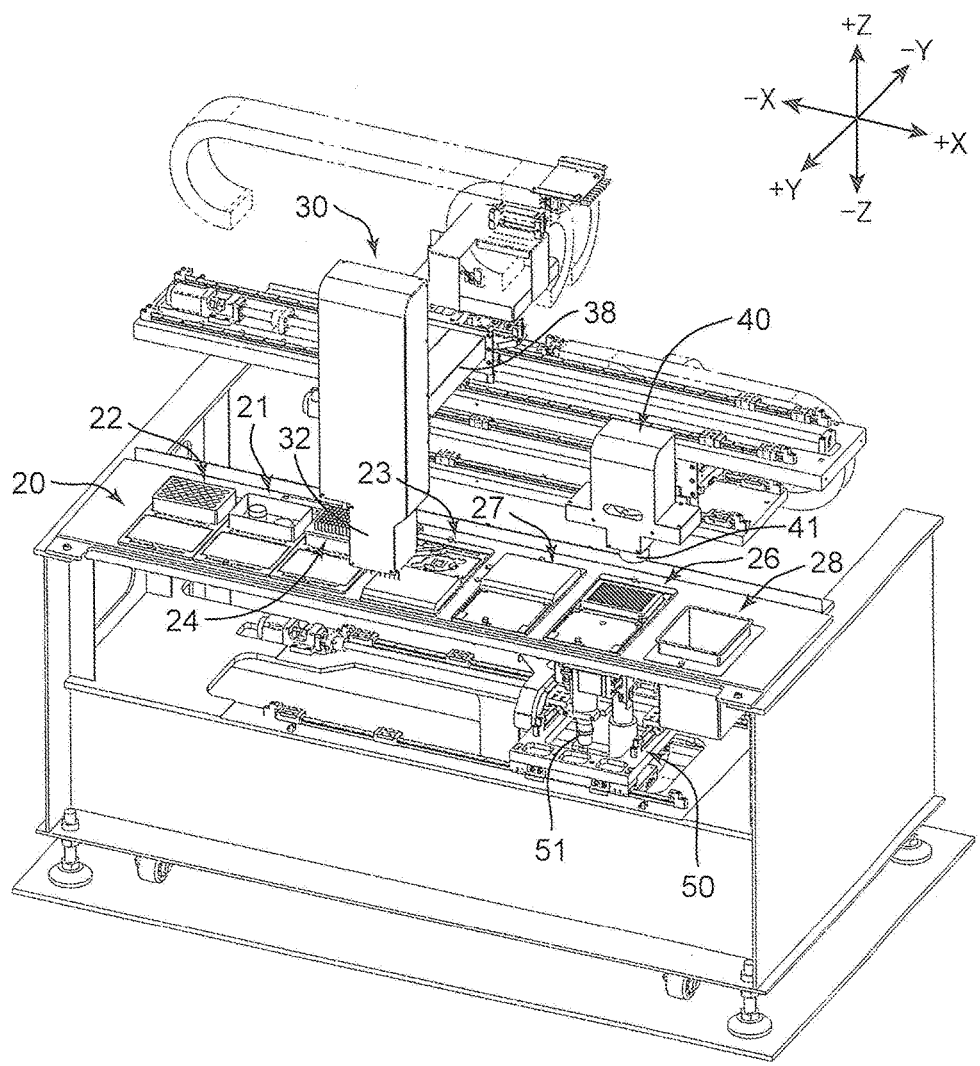
FIG. 27 is a perspective view illustrating one step in the movement work.

FIG. 26 and FIG. 27 are views illustrating how the head unit 30 moves for a cell movement operation in the next cycle. The shaft control unit 162 first moves the head unit 30 located above the tip discarding portion 28 forward (FIG. 26). As a result, the positional relationship in side view between the head unit 30 and the illumination unit 40 is as illustrated in FIG. 3, and the head unit 30 and the illumination unit 40 do not interfere with each other. Next, the shaft control unit 162 moves the head unit 30 along the second path L2 in the left direction so that the head unit 30 approaches the position corresponding to the tip stock portion 24 (FIG. 27). The shaft control unit 162 moves the head unit 30 in the back direction so that the head unit 30 approaches the first path L1 from the second path L2, and stops the head unit 30 above the tip stock portion 24. Then, the shaft control unit 162 lowers the heads 33 all together, and mounts cylinder tips 70 used for the next suction operation to the heads 33.

For fluorescent observation of cell aggregates, a black cover 271 of the black cover placement portion 27 is used. In this case, the shaft control unit 162 moves the head unit 30 to above the black cover placement portion 27, and controls the head drive device 17 to lower the sucking disk head 323 toward the black cover 271. When the sucking disk head 323 abuts on a top surface of the first black cover 271, the shaft control unit 162 causes the second nozzle 322 to generate a suction force so that the black cover 271 is adsorbed by the sucking disk head 323. After that, the shaft control unit 162 moves the head unit 30 to the cell transfer portion 26, and lowers the sucking disk head 323. Accordingly, the microplate 90 is covered with the black cover 271. Then, the shaft control unit 162 stops the suction force of the second nozzle 322 to release the adsorption of the black cover 271 by the sucking disk head 323. In this state, the camera control unit 164 controls the camera 51 to execute fluorescent observation of a cell aggregate carried by the microplate 90. At this time, fluorescent illumination (not shown) mounted to the camera unit 50 is turned on. After the observation, the black cover 271 is returned to the black cover placement portion 27 by the procedure reverse to the above. The same applies to the case of covering the dish 60 with the black cover 271.

The moving device 1 in this embodiment as described above enables the head unit 30 to be moved in the left-right direction by using the first path L1 and the second path L2, with the illumination unit 40, which is required to be moved to follow the camera unit 50, located between the cell sorting portion 23 and the cell transfer portion 26. Specifically, if the illumination unit 40 obstructs the movement of the head unit 30 on the first path L1, the head unit 30 can be bypassed to the second path L2 so that the illumination unit 40 and the head unit 30 pass each other. Consequently, the movement work efficiency for cell aggregates can be remarkably enhanced.

Note that the above-mentioned specific embodiments mainly include the disclosure having the following configurations.

An object moving device according to one aspect of the present disclosure includes: a base; a head unit arranged above the base and including a head that is movable in an up-down direction; an illumination unit arranged above the base and including a light source emitting illumination light; a camera unit arranged below the base and including a camera acquiring an image under the illumination light; and a first drive mechanism configured to move the head unit in a first direction that extends in a horizontal direction and in a second direction that is orthogonal to the first direction in the horizontal direction; a second drive mechanism configured to move the illumination unit in the first direction; a third drive mechanism configured to move the camera unit in the first direction; a control unit configured to control operations of the first, second, and third drive mechanisms; and a movement line including a plurality of workplaces incorporated in the base and arranged in the first direction, the plurality of workplaces including a first container configured to store a moving object therein and a second container configured to receive the moving object, the control unit being configured to: control the first drive mechanism to move the head unit on a first path along the movement line in order to implement at the plurality of workplaces works including a work for moving the moving object between the first container and the second container with use of the head; control the second and third drive mechanisms to move the illumination unit and the camera unit between the first container and the second container on the first path in order to image the first container and the second container; and control, when the head unit and the illumination unit interfere with each other on the first path, the first drive mechanism to move the head unit in the second direction and move the head unit in the first direction on a second path that is side by side with the first path.

According to this moving device, in regard to the head unit and the illumination unit, both of which are arranged above the base, the illumination unit required to move following the camera unit is located between the first container and the second container, and the head unit can be moved in the left-right direction by using the first path and the second path. Specifically, if the head unit interferes with the illumination unit when the head unit is moved on the first path, the head unit can be bypassed to the second path so that the head unit and the illumination unit pass each other. Consequently, object movement work efficiency can be remarkably enhanced.

In the object moving device, it is desired that: the first drive mechanism include a slider configured to reciprocate in the second direction, the head unit be mounted to a distal end of the slider; the first path be arranged on an upstream side of the slider in an advancing direction, and the second path be arranged on a downstream side of the slider in the advancing direction; the illumination unit be arranged between the slider and the base; the slider be configured to move between a first position at which the head unit is positioned with respect to the first path and a second position at which the head unit is positioned with respect to the second path; and the illumination unit be configured to move on the first path without interfering with the head unit in a state in which the slider is located at the second position.

According to this moving device, when the slider is located at the second position, the illumination unit is fitted in a space between the slider and the base. Consequently, the illumination unit is moved on the first path without interfering with the head unit through simple control of moving the slider.

In the object moving device, it is desired that: the first drive mechanism be configured to move the head unit between a first end portion and a second end portion in the first direction; the second drive mechanism be configured to move the illumination unit between a third end portion in the first direction, positioned further toward an inner side than the first end portion, and a fourth end portion in the first direction, positioned further toward an inner side than the second end portion; and the third end portion and the fourth end portion be set at positions at which the illumination unit is prevented from interfering with the head unit even when the illumination unit moves on the first path in a state in which the head unit exists at least the first end portion or the second end portion on the first path.

According to this moving device, the movement range of the illumination unit on the first path is inside the movement range of the head unit. Thus, the head unit can freely move on the first path between workplaces where the illumination unit is not located. Consequently, works can be simultaneously performed by the head unit and the illumination unit.

In this case, it is desired that: the plurality of workplaces in the movement line further comprise: a tip stock portion configured to retain a plurality of tips so that the plurality of tips are mountable to the head, each of the plurality of tips being mountable and removable to and from the head and being configured to suck the moving object and discharge the sucked moving object; and a tip discarding portion configured to collect the tip that has finished the sucking and discharging of the moving object and that has been removed from the head; and the tip stock portion be arranged between the first end portion and the third end portion, and the tip discarding portion be arranged between the second end portion and the fourth end portion.

According to this moving device, the work by the illumination unit and the camera unit and the work by the head unit at the tip stock portion and the tip discarding portion can be simultaneously performed.

In the object moving device, it is desired that: the head have a tip mounted thereto, the tip being configured to suck the moving object and discharge the sucked moving object; and the control unit be configured to implement control of at least one of: control of the first drive mechanism so that the head unit is positioned with the first container via the second path in order to suck the moving object with the tip, and control of the second drive mechanism so that the illumination unit and the camera unit are positioned with respect to the second container in order to image the second container; and control of the first drive mechanism so that the head unit is positioned with the second container via the second path in order to discharge the sucked moving object from the tip, and control of the second drive mechanism so that the illumination unit and the camera unit are positioned with respect to the first container in order to image the first container.

According to this moving device, the head unit can be bypassed to the second path so that the head unit and the illumination unit pass each other, thereby efficiently executing respective works by both the units.

In the moving device, it is desired that: the second drive mechanism be configured to move the illumination unit in the second direction as well; and the third drive mechanism be configured to move the camera unit in the second direction as well. Consequently, the imaging range can be enlarged.

In the object moving device, it is desired that: the head unit include a plurality of the heads; and the control unit be configured to control movement of the plurality of heads in an up-down direction, the control unit being capable of concurrently operating the plurality of the heads.

According to this moving device, the plurality of the heads can be concurrently operated to concurrently execute various works using the heads. Consequently, work efficiency can be improved.

According to the present disclosure described above, the head unit can be moved in the first direction by using the first path and the second path, with the illumination unit, which is required to be moved to follow the camera unit, located between the first container and the second container. Specifically, if the head unit interferes with the illumination unit when the head unit is moved in the first direction on the first path, the head unit can be bypassed to the second path so that the head unit and the illumination unit can pass each other. Consequently, object moving work efficiency can be remarkably enhanced.

The invention claimed is:

1. An object moving device, comprising:
   a base which is formed with translucent material;
   a head unit arranged above the base and including a head that is movable in an up-down direction to aspirate and discharge a moving object;
   an illumination unit arranged above the base and including a light source emitting illumination light;
   a camera unit arranged below the base and including a camera acquiring an image under the illumination light;
   a first drive mechanism configured to move the head unit in a first direction that extends in a horizontal direction and in a second direction that is orthogonal to the first direction in the horizontal direction;
   a second drive mechanism configured to move the illumination unit in the first direction;
   a third drive mechanism configured to move the camera unit in the first direction;
   a control unit configured to control operations of the first, second, and third drive mechanisms; and
   a movement line including a first container configured to store the moving object therein and a second container configured to receive the moving object, the first container and the second container being incorporated in the base and arranged in the first direction; wherein
   the control unit is further configured to:
      control the first drive mechanism to move the head unit on a first path along the movement line in order to implement at a plurality of works including a work for moving the moving object between the first container and the second container with use of the head;
      control the second and third drive mechanisms to move the illumination unit and the camera unit between the first container and the second container on the first path in order to image the first container and the second container; and
      control, when the head unit and the illumination unit interfere with each other on the first path, the first drive mechanism to move the head unit in the second direction and move the head unit in the first direction on a second path that is side by side with the first path.

2. The object moving device according to claim 1, wherein:
   the first drive mechanism is configured to reciprocate in the second direction;
   the head unit is mounted to a distal end of the first drive mechanism;
   the first path is arranged on an upstream side of the first drive mechanism in an advancing direction, and the second path is arranged on a downstream side of the first drive mechanism in the advancing direction;
   the illumination unit is arranged between the first drive mechanism and the base;
   the first drive mechanism is configured to move between a first position at which the head unit is positioned with respect to the first path and a second position at which the head unit is positioned with respect to the second path; and
   the illumination unit is configured to move on the first path without interfering with the head unit in a state in which the first drive mechanism is located at the second position.

3. The object moving device according to claim 1, wherein
   the first drive mechanism is configured to move the head unit between a first end portion and a second end portion in the first direction;
   the second drive mechanism is configured to move the illumination unit between a third end portion in the first direction, positioned further toward an inner side than the first end portion, and a fourth end portion in the first direction, positioned further toward an inner side than the second end portion; and
   the third end portion and the fourth end portion are set at positions at which the illumination unit is prevented from interfering with the head unit even when the illumination unit moves on the first path in a state in which the head unit exists at least the first end portion or the second end portion on the first path.

4. The object moving device according to claim 3, wherein:
   the movement line further includes other workplaces incorporated in the base and arranged in the first direction;
   the other workplaces include:
      a tip stock portion configured to retain a plurality of tips so that the plurality of tips are mountable to the head, each of the plurality of tips being mountable and removable to and from the head and being configured to suck the moving object and discharge the sucked moving object; and
      a tip discarding portion configured to collect the tip that has finished the sucking and discharging of the moving object and that has been removed from the head; and
   the tip stock portion is arranged between the first end portion and the third end portion, and the tip discarding portion is arranged between the second end portion and the fourth end portion.

5. The object moving device according to claim 1, wherein
   the head has a tip mounted thereto, the tip being configured to suck the moving object and discharge the sucked moving object; and the control unit is configured to implement control of at least one of:
  control of the first drive mechanism so that the head unit is positioned with respect to the first container via the second path in order to suck the moving object with the tip, and control of the second drive mechanism so that the illumination unit and the camera unit are positioned with respect to the second container in order to image the second container; and
  control of the first drive mechanism so that the head unit is positioned with respect to the second container via the second path in order to discharge the sucked moving object from the tip, and control of the second drive mechanism so that the illumination unit and the camera unit are positioned with respect to the first container in order to image the first container.

6. The object moving device according to claim 1, wherein
  the second drive mechanism is configured to move the illumination unit in the second direction as well; and
  the third drive mechanism is configured to move the camera unit in the second direction as well.

7. The object moving device according to claim 1, wherein
  the head unit includes a plurality of heads; and
  the control unit is configured to control movement of the plurality of the heads in an up-down direction, the control unit being capable of concurrently operating the plurality of the heads.

* * * * *